US007932371B2

(12) United States Patent
Brandt

(10) Patent No.: US 7,932,371 B2
(45) Date of Patent: Apr. 26, 2011

(54) TICK OCTOPAMINE RECEPTOR NUCLEIC ACID MOLECULES

(75) Inventor: Kevin S. Brandt, Longmont, CO (US)

(73) Assignee: Heska Corporation, Loveland, CO (US)

( * ) Notice: Subject to any disclaimer, the term of this patent is extended or adjusted under 35 U.S.C. 154(b) by 16 days.

(21) Appl. No.: 12/200,456

(22) Filed: Aug. 28, 2008

(65) Prior Publication Data

US 2009/0017494 A1 Jan. 15, 2009

Related U.S. Application Data

(62) Division of application No. 10/521,162, filed as application No. PCT/US03/21706 on Jul. 11, 2003, now Pat. No. 7,419,793.

(60) Provisional application No. 60/426,601, filed on Nov. 15, 2002, provisional application No. 60/319,402, filed on Jul. 17, 2002.

(51) Int. Cl.
*C12N 5/12* (2006.01)
*C12N 15/63* (2006.01)
*C12N 1/21* (2006.01)
*C12N 1/15* (2006.01)
*C12N 5/10* (2006.01)
*C07K 14/705* (2006.01)
*G01N 33/566* (2006.01)

(52) U.S. Cl. .................. 536/23.5; 435/320.1; 435/252.3; 435/254.11; 435/325; 435/410; 435/7.2; 530/350

(58) Field of Classification Search ......................... None
See application file for complete search history.

(56) References Cited

U.S. PATENT DOCUMENTS

| 5,344,776 A | 9/1994 | Venter et al. |
| 5,474,898 A | 12/1995 | Venter et al. |
| 6,063,610 A | 5/2000 | Silver et al. |
| 7,419,793 B2 | 9/2008 | Brandt |

FOREIGN PATENT DOCUMENTS

| WO | WO 99/21891 | 5/1999 |
| WO | WO 00/61621 | 10/2000 |

OTHER PUBLICATIONS

Isoai et al (1996. Gene. 175: 95-100).*
Chen et al, 2007. Veterinary Parasitology. 148: 379-383.*
Blenau et al, 2001. Archives of Insect Biochemistry and Physiology. 48: 13-38.*
Evans P D and Robb S: "Octopamine Receptor Subtypes and Their Modes of Action" Neurochemical Research, Plenum Press, New York, US, vol. 18, No. 8, Aug. 1993, pp. 869-874.
"Drosophila melanogaster octopamine receptor OAMB Mrna, complete cds", GenBank Accession No. AF065443, http://www.ncbi.nlm.nih.gov/nuccore/3153890, accessed Mar. 19, 2009.
"Probable G-protein coupled receptor No9", GenBank Accession No. Q93126, http://www.ncbi.nlm.nih.gov/protein, Date: Mar. 3, 2009.
Van Poyer et al., "Phenolamine-dependent adenylyl cyclase activation in Drosophila Schneider 2 cells", Insect Biochemistry and Molecular Biology, 31 (2001) 333-338.
Official Action for U.S. Appl. No. 10/521,162, mailed Apr. 19, 2007.
Official Action for U.S. Appl. No. 10/521,162, mailed Jul. 16, 2007.
Official Action for U.S. Appl. No. 10/521,162, mailed Dec. 28, 2007.
Notice of Allowance for U.S. Appl. No. 10/521,162, mailed Apr. 25, 2008.
Arakawa, et al., "Neuron," 1990, vol. 2, pp. 343-354.
Baxter, et al., "Insect Biochemistry and Molecular Biology," 1999, vol. 29, pp. 461-467.
Gen Bank Accession No. D78587, Isoai, et al., 1999.
Gen Bank Accession No. BAA11424, lsoai, et al., 1999.
Han, et al., "The Journal of Neuroscience," 1998, vol. 18, No. 10, pp. 3650-3658.
Han, et al., "Neuron," 1996, vol. 16, pp. 1127-1135.
Saudou, et al., "The EMBO Journal," 1990, vol. 9, No. 11, pp. 3611-3617.
Wells, Sep. 18, 1990, "Biochemistry," 29(37: 8509-8517.
Ngo, et al., Mar. 1994, "The Protein Folding Problem and Tertiary Structure Prediction, Chapter 14: Computational Complexity Protein Structure Prediction, and the Levinthal Paradox," pp. 492-495.
Bork, 2000, "Genome Research," 10: 398.
Skolnick and Fetrow, 2000, "Trends in Biotech," 18(1): 34.
Doerks et al., Jun. 1998, "Trends in Genetics," 14(6): 248.
Smith and Zhang, Nov. 1997, "Nature Biotechnology," 15: 1222.
Brenner, Apr. 1999, "Trends in Genetics," 15(4): 132.
Bork and Bairoch, Oct. 1996, "Trends in Genetics," 12(10): 425.
Wang et al., 1999, "Nuc Acids Res," 27: 4609-4618.
Kaufman et al., 1999, "Blood," 94: 3178-3184.
Gaines, et al., "Analysis of expressed sequence tags from subtracted and unsubtracted *Ctenocephalides felis* hindgut and Malpighian tubule cDNA libraries," *Insect Molecular Biology*, 11(4): 299-308, 2002.
Reeves, et al., "Cloning and sequence analysis of the alpha subunit of the cat flea sodium pump," *Insect Biochem Mol Biol.*, Oct; 23(7): 809-14 1993.
Mita, et al., "Establishment of cDNA database of *Bombyx mori*," EBI Accession No. AU003320, Jan. 19, 1999.

* cited by examiner

*Primary Examiner* — Bridget E Bunner
*Assistant Examiner* — Zachary C Howard
(74) *Attorney, Agent, or Firm* — Sheridan Ross P.C.

(57) ABSTRACT

The present invention relates to tick octopamine receptor nucleic acid molecules; to tick octopamine receptor proteins encoded by such nucleic acid molecules; to antibodies raised against such proteins; and to compounds that inhibit the activity of such proteins. The present invention also includes methods to obtain such proteins, nucleic acid molecules, antibodies, and inhibitory compounds. The present invention also includes inhibitory compounds, particularly those that specifically inhibit tick octopamine receptor activity, as well as the use of such compounds to treat animals.

7 Claims, No Drawings

TICK OCTOPAMINE RECEPTOR NUCLEIC ACID MOLECULES

CROSS-REFERENCE TO RELATED APPLICATIONS

This application is a divisional of U.S. patent application Ser. No. 10/521,162, filed Jan. 13, 2005, entitled "FLEA OCTOPAMINE RECEPTOR NUCLEIC ACID MOLECULES, PROTEINS AND USES THEREOF", which issued as U.S. Pat. No. 7,419,793 on Sep. 2, 2009; which claims priority to international PCT Application No. PCT/US03/21706, filed Jul. 11, 2003, entitled "FLEA AND TICK OCTOPAMINE RECEPTOR NUCLEIC ACID MOLECULES"; which claims priority to U.S. Provisional Patent Application Ser. No. 60/426,601, filed Nov. 15, 2002, entitled "TICK OCTOPAMINE RECEPTOR NUCLEIC ACID MOLECULES, PROTEINS AND USES THEREOF"; and U.S. Provisional Patent Application Ser. No. 60/319,402, filed Jul. 17, 2002, entitled "FLEA OCTOPAMINE RECEPTOR NUCLEIC ACID MOLECULES".

FIELD OF THE INVENTION

The present invention relates to flea and tick octopamine receptor nucleic acid molecules, proteins encoded by such nucleic acid molecules, antibodies raised against such proteins, and inhibitors of such proteins. The present invention also includes methods to obtain such proteins, nucleic acid molecules, antibodies, and inhibitory compounds. The present invention also includes therapeutic compositions comprising such inhibitors, as well as uses thereof.

BACKGROUND OF THE INVENTION

Flea and tick infestation of animals is a health and economic concern for pet owners. Fleas and ticks are known to carry a variety of infectious agents including, but not limited to bacteria, viruses, protozoan parasites, and *rickettsia*. As such, fleas and ticks are a problem not only when they are on an animal but also when they are in the general environment of the animal.

The medical importance of flea and tick infestation has prompted the development of reagents capable of controlling flea and/or tick infestation. Commonly encountered methods to control infestation are generally focused on use of insecticides, which are often unsuccessful for one or more of the following reasons: (1) failure of owner compliance (frequent administration is required); (2) behavioral or physiological intolerance of the pet to the pesticide product or means of administration; and (3) the emergence of flea and/or tick populations resistant to the prescribed dose of pesticide.

Octopamine receptor is a member of the biogenic amine receptor family, which also includes receptors for dopamine, serotonin, and tyramine. Octopamine is a major neuromodulator in insects with neurotransmitter and neurohormone functions and is a known activator of adenylate cyclase, resulting in stimulation of cyclic AMP production.

Prior investigations have described certain insect biogenic amine receptors in *Drosophila melanogaster*, including for example, Arakawa et al. 1990, *Neuron*, 2:343-354, Venter et al., U.S. Pat. No. 5,474,898, Saudou et al., 1990, *EMBO Journal*, 9(11):3611-3617, and Han et al., 1998, *J. Neuroscience*, 18(10):3650-3658. Unfortunately, members of the biogenic amine receptor family have proven difficult to clone due to the rarity of the sequence as cDNA and often have highly related sequences and activities, which has resulted in confusion in the art with respect to the true identity of reported sequences.

Insect octopamine receptor is a known target of various insecticides, including formamadine compounds such as demethylchlordimeform (DCDM). However, no formamadine compound to date has been shown to be safe and efficacious for use for treating tick infestations on a host animal. Octopamine receptor is not present in vertebrates and within insects susceptibility to insecticides targeting the octopamine receptor have been shown to vary by species. Therefore, in order to create compounds and treatments which are efficacious against fleas and/or ticks while minimizing toxicity to the host animal or to non-target insects, it would be a distinct advantage to have the sequence of the flea and/or tick octopamine receptor. Accordingly, isolation and sequencing of flea and/or tick octopamine receptor genes may be critical for use in identifying specific agents for treating animals for infestation.

SUMMARY OF THE INVENTION

The present invention provides flea and tick octopamine receptor proteins; nucleic acid molecules encoding flea and tick octopamine receptor proteins; antibodies raised against such proteins (i.e., anti-flea and anti-tick octopamine receptor antibodies); mimetopes of such proteins or antibodies; and compounds that inhibit flea and/or tick octopamine receptor activity (i.e. inhibitory compounds or inhibitors).

The present invention also includes methods to obtain such proteins, mimetopes, nucleic acid molecules, antibodies and inhibitory compounds. The present invention also includes the use of proteins and antibodies to identify such inhibitory compounds as well as assay kits to identify such inhibitory compounds. Also included in the present invention are therapeutic compositions comprising proteins, mimetopes, nucleic acid molecules, antibodies and inhibitory compounds of the present invention including therapeutic compounds derived from a protein of the present invention that inhibit the activity of flea and/or tick octopamine receptor proteins.

One embodiment of the present invention is an isolated octopamine receptor nucleic acid molecule that hybridizes with a nucleic acid sequence having SEQ ID NO:2, SEQ ID NO:5, SEQ ID NO:8, SEQ ID NO:13, SEQ ID NO:32, SEQ ID NO:35, SEQ ID NO:38 or SEQ ID NO:41, under conditions that allow less than or equal to 5% base pair mismatch, wherein such nucleic acid molecule encodes a protein that binds octopamine, or a nucleic acid molecule having a sequence fully complementary to such a nucleic acid molecule.

Another embodiment of the present invention is an isolated octopamine receptor nucleic acid molecule having a nucleic acid sequence that is at least 95% identical to SEQ ID NO:1, SEQ ID NO:2, SEQ ID NO:3, SEQ ID NO:5, SEQ ID NO:6, SEQ ID NO:8, SEQ ID NO:11, SEQ ID NO:13, SEQ ID NO:30, SEQ ID NO:32, SEQ ID NO:33, SEQ ID NO:35, SEQ ID NO:36, SEQ ID NO:38, SEQ ID NO:39 or SEQ ID NO:41 or a fragment thereof that encodes a protein that binds octopamine. Another embodiment of the present invention is an isolated octopamine receptor nucleic acid molecule that encodes a protein that is at least 95% identical to SEQ ID NO:4, SEQ ID NO:7, SEQ ID NO:12, SEQ ID NO:31, SEQ ID NO:34, SEQ ID NO:37 or SEQ ID NO:40, or a fragment thereof that encodes a protein that binds octopamine, or a nucleic acid sequence fully complementary to such a nucleic acid sequence.

The present invention also relates to recombinant molecules, recombinant viruses and recombinant cells that include a nucleic acid molecule of the present invention. Also included are methods to produce such nucleic acid molecules, recombinant molecules, recombinant viruses and recombinant cells. Also included are methods to produce a protein of the present invention.

Another embodiment of the present invention includes an isolated octopamine receptor protein that is at least 95% identical to an amino acid sequence selected from the group consisting of SEQ ID NO:4, SEQ ID NO:7, SEQ ID NO:12, SEQ ID NO:31, SEQ ID NO:34, SEQ ID NO:37 and SEQ ID NO:40, wherein such protein binds to octopamine.

Another embodiment of the present invention includes an isolated octopamine receptor protein encoded by a nucleic acid molecule that hybridizes with a nucleic acid sequence having SEQ ID NO:2, SEQ ID NO:5, SEQ ID NO:8, SEQ ID NO:13, SEQ ID NO:32, SEQ ID NO:35, SEQ ID NO:38 or SEQ ID NO:41, under conditions that allow less than or equal to 5% base pair mismatch.

Another embodiment of the present invention includes a method to detect an inhibitor of flea or tick octopamine receptor activity, said method comprising (a) contacting an isolated flea or tick octopamine receptor protein of the present invention, with a putative inhibitory compound under conditions in which, in the absence of said compound, said protein has flea or tick octopamine receptor protein activity, and (b) determining if said putative inhibitory compound inhibits flea or tick octopamine receptor protein activity.

DETAILED DESCRIPTION OF THE INVENTION

The present invention provides for flea and tick octopamine receptor nucleic acid molecules, proteins encoded by such nucleic acid molecules, antibodies raised against such proteins, and inhibitors of such proteins. As used herein, flea and tick octopamine receptor nucleic acid molecules and proteins encoded by such nucleic acid molecules are also referred to as octopamine receptor nucleic acid molecules and proteins of the present invention, respectively. Flea and tick octopamine receptor nucleic acid molecules and proteins of the present invention can be isolated from a flea or tick or prepared recombinantly or synthetically. Flea and tick octopamine receptor nucleic acid molecules of the present invention can be RNA or DNA, or modified forms thereof, and can be double-stranded or single-stranded; examples of nucleic acid molecules include, but are not limited to, complementary DNA (cDNA) molecules, genomic DNA molecules, synthetic DNA molecules, DNA molecules which are specific tags for messenger RNA, and corresponding mRNA molecules. As such, a flea or tick nucleic acid molecule of the present invention is not intended to refer to an entire chromosome within which such a nucleic acid molecule is contained, however, a flea or tick octopamine receptor nucleic acid molecule of the present invention may include all regions such as regulatory regions that control production of octopamine receptor proteins encoded by such a nucleic acid molecule (such as, but not limited to, transcription, translation or post-translation control regions) as well as the coding region itself, and any introns or non-translated coding regions. As used herein, the phrase "tick octopamine receptor protein" refers to a protein encoded by a tick octopamine receptor nucleic acid molecule and the phrase "flea octopamine receptor protein" refers to a protein encoded by a flea octopamine receptor nucleic acid molecule.

Tick octopamine receptor nucleic acid molecules of known length isolated from a tick, such as *Rhipicephalus sanguineus* are denoted "nRsOCR$_{\#}$", for example nRsOCR$_{1443}$, wherein "#" refers to the number of nucleotides in that molecule, and tick octopamine receptor proteins of known length are denoted "PRsOCR$_{\#}$" (for example PRsOCR$_{480}$) wherein "#" refers to the number of amino acid residues in that molecule. Flea octopamine receptor nucleic acid molecules of known length isolated from a flea, such as *Ctenocephalides felis* are denoted "nCfOCR$_{\#}$", for example nCfOCR$_{2136}$, wherein "#" refers to the number of nucleotides in that molecule, and flea octopamine receptor proteins of known length are denoted "PCfOCR$_{\#}$" (for example PCfOCR$_{712}$) wherein "#" refers to the number of amino acid residues in that molecule.

The present invention also provides for flea and/or tick octopamine receptor DNA molecules that are specific tags for messenger RNA molecules. Such DNA molecules can correspond to an entire or partial sequence of a messenger RNA, and therefore, a DNA molecule corresponding to such a messenger RNA molecule (i.e. a cDNA molecule), can encode a full-length or partial-length protein. A nucleic acid molecule encoding a partial-length protein can be used directly as a probe or indirectly to generate primers to identify and/or isolate a cDNA nucleic acid molecule encoding a corresponding, or structurally related, full-length protein. A cDNA encoding a partial-length octopamine receptor protein can also be used in a similar manner to identify a genomic nucleic acid molecule, such as a nucleic acid molecule that contains the complete gene including regulatory regions, exons and introns. Methods for using cDNA molecules and sequences encoding partial-length flea or tick octopamine receptor proteins to isolate nucleic acid molecules encoding full-length flea or tick octopamine receptor proteins and corresponding cDNA molecules are described in the examples herein below.

The proteins and nucleic acid molecules of the present invention can be obtained from their natural source, or can be produced using, for example, recombinant nucleic acid technology or chemical synthesis. Also included in the present invention is the use of these proteins and nucleic acid molecules as well as antibodies and inhibitory compounds thereto as therapeutic compositions, as well as in other applications, such as those disclosed below.

One embodiment of the present invention is an isolated protein that includes a flea and/or tick octopamine receptor protein. It is to be noted that the term "a" or "an" entity refers to one or more of that entity; for example, a protein, a nucleic acid molecule, an antibody and a therapeutic composition refers to "one or more" or "at least one" protein, nucleic acid molecule, antibody and therapeutic composition respectively. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, isolated flea and tick octopamine receptor proteins of the present invention can be full-length proteins or any homologue of such proteins. An isolated protein of the present invention, including a homologue, can be identified in a straight-forward manner by the protein's ability to elicit an immune response against a flea or tick octopamine receptor protein or by the protein's ability to exhibit flea or tick octopamine receptor activity, e.g. the ability to bind to octopamine. Examples of flea and tick octopamine receptor homologue proteins include flea and tick octopamine receptor proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue includes at least one epitope capable of eliciting an immune response against a flea and/or tick octopamine receptor protein, and/or of binding to an antibody directed against a flea and/or tick octopamine receptor protein. That is, when the homologue is administered to an animal as an immunogen, using techniques known to those skilled in the art, the animal will produce an immune response against at least one epitope of a natural flea and/or tick octopamine receptor protein. The ability of a protein to effect an immune response can be measured using techniques known to those skilled in the art. As used herein, the term "epitope" refers to the smallest portion of a protein or other antigen capable of selectively binding to the antigen binding site of an antibody or a T cell receptor. It is well accepted by those skilled in the art that the minimal size of a protein epitope is about four to six amino acids. As is appreciated by those skilled in the art, an epitope can include amino acids that naturally are contiguous to each other as well as amino acids that, due to the tertiary structure of the natural protein, are in sufficiently close proximity to form an epitope. According to the present invention, an epitope includes a portion of a protein comprising at least 4 amino acids, at least 5 amino acids, at least 6 amino acids, at least 10 amino acids, at least 15 amino acids, at least 20 amino acids, at least 25 amino acids, at least 30 amino acids, at least 35 amino acids, at least 40 amino acids or at least 50 amino acids in length.

In one embodiment of the present invention a flea or tick octopamine receptor homologue protein has flea or tick octopamine receptor activity, respectively, i.e. the homologue exhibits an activity similar to its natural counterpart, e.g. the ability to bind octopamine. Methods to detect and measure such activities are known to those skilled in the art.

Flea and tick octopamine receptor homologue proteins can be the result of natural allelic variation or natural mutation. Flea and tick octopamine receptor protein homologues of the present invention can also be produced using techniques known in the art including, but not limited to, direct modifications to the protein or modifications to the gene encoding the protein using, for example, classic or recombinant DNA techniques to effect random or targeted mutagenesis.

Flea and tick octopamine receptor proteins of the present invention are encoded by flea and tick octopamine receptor nucleic acid molecules, respectively. As used herein, flea and/or tick octopamine receptor nucleic acid molecules include nucleic acid sequences related to natural octopamine receptor genes, and, preferably, to $C.$ $felis$ and $R.$ $sanguineus$ tick octopamine receptor genes, respectively. As used herein, flea and tick octopamine receptor genes include all regions such as regulatory regions that control production of flea and tick octopamine receptor proteins encoded by such genes (such as, but not limited to, transcription, translation or post-translation control regions) as well as the coding region itself, and any introns or non-translated coding regions. As used herein, a nucleic acid molecule that "includes" or "comprises" a sequence may include that sequence in one contiguous array, or may include the sequence as fragmented exons such as is often found for a tick gene. As used herein, the term "coding region" refers to a continuous linear array of nucleotides that translates into a protein. A full-length coding region is that coding region that is translated into a full-length, i.e., a complete protein as would be initially translated in its natural millieu, prior to any post-translational modifications.

One embodiment of the present invention is a $C.$ $felis$ flea octopamine receptor gene that includes the nucleic acid sequence SEQ ID NO:1, SEQ ID NO:2, SEQ ID NO:3, SEQ ID NO:5, SEQ ID NO:6, SEQ ID NO:8, SEQ ID NO:11 and SEQ ID NO:13 and a $R.$ $sanguineus$ tick octopamine receptor gene that includes the nucleic acid sequence SEQ ID NO:30, SEQ ID NO:32, SEQ ID NO:33, SEQ ID NO:35, SEQ ID NO:36, SEQ ID NO:38, SEQ ID NO:39, and SEQ ID NO:41 either in a consecutive array or interrupted by naturally occurring introns. These nucleic acid sequences are further described herein. For example, nucleic acid sequence SEQ ID NO:39 represents the deduced sequence of the coding strand of a $R.$ $sanguineus$ cDNA denoted herein as $R.$ $sanguineus$ octopamine receptor nucleic acid molecule $nRsOCR_{1443}$, the production of which is disclosed in the Examples. Nucleic acid molecule SEQ ID NO:39 comprises an apparently full-length coding region. The complement of SEQ ID NO:39 (represented herein by SEQ ID NO:41) refers to the nucleic acid sequence of the strand fully complementary to the strand having SEQ ID NO:39, which can easily be determined by those skilled in the art. Likewise, a nucleic acid sequence complement of any nucleic acid sequence of the present invention refers to the nucleic acid sequence of the nucleic acid strand that is fully complementary to (i.e., can form a complete double helix with) the strand for which the sequence is cited. It should be noted that since nucleic acid sequencing technology is not entirely error-free, SEQ ID NO:39 (as well as other nucleic acid and protein sequences presented herein) represents an apparent nucleic acid sequence of the nucleic acid molecule encoding a tick octopamine receptor protein of the present invention.

Translation of SEQ ID NO:39, the coding strand of $nRsOCR_{1443}$ yields a protein of 480 amino acids, denoted herein as $PRsOCR_{480}$, the amino acid sequence of which is presented in SEQ ID NO:40, assuming an (a) initiation codon extending from nucleotide 1 to 3 of SEQ ID NO:39 and (b) a last codon extending from nucleotide 1 to 1440 of SEQ ID NO:39.

Translation of SEQ ID NO:11, the coding strand of $nCfOCR_{2136}$ yields a protein of 712 amino acids, denoted herein as $PCfOCR_{712}$, the amino acid sequence of which is presented in SEQ ID NO:12, assuming an (a) initiation codon extending from nucleotide 1 to 3 of SEQ ID NO:11 and (b) a last codon extending from nucleotide 2134 to 2136 of SEQ ID NO:11.

In one embodiment, a gene or other nucleic acid molecule of the present invention can be an allelic variant that includes a similar but not identical sequence to SEQ ID NO:1, SEQ ID NO:2, SEQ ID NO:3, SEQ ID NO:5, SEQ ID NO:6, SEQ ID NO:8, SEQ ID NO:11, SEQ ID NO:13, SEQ ID NO:30, SEQ ID NO:32, SEQ ID NO:33, SEQ ID NO:35, SEQ ID NO:36, SEQ ID NO:38, SEQ ID NO:39, and SEQ ID NO:41. For example, an allelic variant of a $C.$ $felis$ octopamine receptor gene including SEQ ID NO:1, SEQ ID NO:2, SEQ ID NO:3, SEQ ID NO:5, SEQ ID NO:6, SEQ ID NO:8, SEQ ID NO:11 and SEQ ID NO:13, is a gene that occurs at essentially the same locus (or loci) in the genome as the gene including SEQ ID NO:1, SEQ ID NO:2, SEQ ID NO:3, SEQ ID NO:5, SEQ ID NO:6, SEQ ID NO:8, SEQ ID NO:11 and SEQ ID NO:13 and an allelic variant of a $R.$ $sanguineus$ octopamine receptor gene including SEQ ID NO:30, SEQ ID NO:32, SEQ ID NO:33, SEQ ID NO:35, SEQ ID NO:36, SEQ ID NO:38, SEQ ID NO:39, and SEQ ID NO:41, is a gene that occurs at essentially the same locus (or loci) in the genome as the gene including SEQ ID NO:30, SEQ ID NO:32, SEQ ID NO:33, SEQ ID NO:35, SEQ ID NO:36, SEQ ID NO:38, SEQ ID NO:39, and SEQ ID NO:41, but which, due to natural variations caused by, for example, mutation or recombination, has a similar but not identical sequence. Because natural selection typically selects against alterations that affect function, allelic variants (i.e. alleles corresponding to, or of, cited nucleic acid sequences) usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to occur naturally within a given tick species, since the genome is diploid, and sexual reproduction will result in the reassortment of alleles.

In one embodiment of the present invention, isolated flea or tick octopamine receptor proteins are encoded by nucleic acid molecules that hybridize under stringent hybridization conditions to genes or other nucleic acid molecules encoding flea or tick octopamine receptor proteins, respectively. The minimal size of flea or tick octopamine receptor proteins of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the flea or tick octopamine receptor nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding a flea or tick octopamine receptor protein is at least about 12 to about 15 nucleotides in length if the nucleic acid molecule is GC-rich and at least about 15 to about 17 bases in length if it is AT-rich. The minimal size of a nucleic acid molecule used to encode a flea or tick octopamine receptor protein homologue of the present invention is from about 12 to about 18 nucleotides in length. Thus, the minimal size of flea or tick octopamine receptor protein homologues of the present invention is from about 4 to about 6 amino acids in length. There is no limit, other than a practical limit on the maximal size of a nucleic acid molecule encoding a flea or tick octopamine receptor protein of the present invention because a nucleic acid molecule of the present invention can include a portion of a gene or cDNA or RNA, an entire gene or cDNA or RNA, or multiple genes or cDNA or RNA. The preferred size of a protein encoded by a nucleic acid molecule of the present invention depends on whether a full-length, fusion, multivalent, or functional portion of such a protein is desired.

Stringent hybridization conditions are determined based on defined physical properties of the flea or tick octopamine receptor nucleic acid molecule to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al, 1989, *Molecular Cloning: A Laboratory Manual*, Cold Spring Harbor Labs Press, and Meinkoth, et at., 1984, *Anal. Biochem.* 138, 267-284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m=81.5°\ C.+16.6\ \log M+0.41(\%G+C)-500/n-0.61(\%\ \text{formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d=4(G+C)+2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with greater than a specified % base pair mismatch will hybridize. Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under conditions that would allow less than or equal to 30% pair mismatch with a flea or tick octopamine receptor nucleic acid molecule of about 150 bp in length or greater, the following conditions could preferably be used. The average G+C content of tick DNA is about 30% and the average G+C content of flea DNA is about 37%, as calculated from known tick nucleic acid sequences. The unknown nucleic acid molecules would be attached to a support membrane, and the 150 bp probe would be labeled, e.g. with a radioactive tag. The hybridization reaction could be carried out in a solution comprising 2×SSC in the absence of nucleic acid helix destabilizing compounds, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. The skilled artisan would calculate the washing conditions required to allow up to 30% base pair mismatch. For example, in conducting a hybridization of tick DNA, in a wash solution comprising 1×SSC in the absence of nucleic acid helix destabilizing compounds, the $T_m$ of perfect hybrids would be about 76.8° C.:

$$81.5° C.+16.6 \log(0.15M)+(0.41×30)-(500/150)-(0.61×0)=76.8° C.$$

Thus, to achieve hybridization with nucleic acid molecules having about 20% base pair mismatch, hybridization washes would be carried out at a temperature of less than or equal to 56.8° C. To calculate the washing conditions for a hybridization with flea DNA, the artisan would adjust the formula due to the difference in G+C content of flea compared to tick to arrive at a wash temperature of 79.6° C. It is thus within the skill of one in the art to calculate additional hybridization temperatures based on the desired percentage base pair mismatch, formulae and G/C content disclosed herein. For example, it is appreciated by one skilled in the art that as a nucleic acid molecule to be tested for hybridization against tick nucleic acid molecules of the present invention having sequences specified herein becomes longer than 150 nucleotides, the $T_m$ for a hybridization reaction allowing up to 20% base pair mismatch will not vary significantly from 56.8° C. Similarly, to achieve hybridization with nucleic acid molecules having about 10% base pair mismatch, hybridization washes would be carried out at a temperature of less than or equal to 66.8° C. and to achieve hybridization with nucleic acid molecules having about 5% base pair mismatch, hybridization washes would be carried out at a temperature of less than or equal to 71.8° C.

Furthermore, it is known in the art that there are commercially available computer programs for determining the degree of similarity between two nucleic acid or protein sequences. These computer programs include various known methods to determine the percentage identity and the number and length of gaps between hybrid nucleic acid molecules or proteins. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, the SeqLab® Wisconsin Package™ Version 10.0-UNIX sequence analysis software, available from Genetics Computer Group, Madison, Wis. (hereinafter "SeqLab"); and DNAsis® sequence analysis software, version 2.0, available from Hitachi Software, San Bruno, Calif. (hereinafter "DNAsis"). Such software programs represent a collection of algorithms paired with a graphical user interface for using the algorithms. The DNAsis and SeqLab software, for example, employ a particular algorithm, the Needleman-Wunsch algorithm to perform pair-wise comparisons between two sequences to yield a percentage identity score, see Needleman, S. B. and Wunch, C. D., 1970, *J. Mol. Biol.*, 48, 443, which is incorporated herein by reference in its entirety. Such algorithms, including the Needleman-Wunsch algorithm, are commonly used by those skilled in the nucleic acid and amino acid sequencing art to compare sequences. A preferred method to determine percent identity among amino acid sequences and also among nucleic acid sequences includes using the Needleman-Wunsch algorithm, available in the SeqLab software, using the Pairwise Comparison/Gap function with the nwsgapdna.cmp scoring matrix, the gap creation penalty and the gap extension penalties set at default values, and the gap shift limits set at maximum (hereinafter referred to as "SeqLab default parameters"). An additional preferred method to determine percent identity among amino acid sequences and also among nucleic acid sequences includes using the Higgins-Sharp algorithm, available in the DNAsis software (hereinafter "DNAsis"), with the gap penalty set at 5, the number of top diagonals set at 5, the fixed gap penalty set at 10, the k-tuple set at 2, the window size set at 5, and the floating gap penalty set at 10. A particularly preferred method to determine percent identity among amino acid sequences and also among nucleic acid sequences includes using the Needleman-Wunsch algorithm available in the SeqLab software, using the SeqLab default parameters.

One embodiment of the present invention includes flea and tick octopamine receptor proteins. Preferred flea and tick octopamine receptor proteins include proteins encoded by a nucleic acid molecule that hybridizes under conditions that preferably allow less than or equal to 30% base pair mismatch, preferably under conditions that allow less than or equal to 20% base pair mismatch, preferably under conditions that allow less than or equal to 10% base pair mismatch, preferably under conditions that allow less than or equal to 8% base pair mismatch, preferably under conditions that allow less than or equal to 5% base pair mismatch or preferably under conditions that allow less than or equal to 2% base pair mismatch with a nucleic acid molecule selected from the group consisting of SEQ ID NO:2, SEQ ID NO:5, SEQ ID NO:8, SEQ ID NO:13, SEQ ID NO:32, SEQ ID NO:35, SEQ ID NO:38 and SEQ ID NO:41.

Another embodiment of the present invention includes a flea octopamine receptor protein encoded by a nucleic acid molecule that hybridizes under conditions comprising, (a) hybridizing in a solution comprising 1×SSC in the absence of nucleic acid helix destabilizing compounds, at a temperature of 37° C. and (b) washing in a solution comprising 1×SSC in the absence of nucleic acid helix destabilizing compounds, at a temperature of 49.6° C., to an isolated nucleic acid molecule selected from the group consisting of SEQ ID NO:2, SEQ ID NO:5, SEQ ID NO:8 and SEQ ID NO:13.

Another embodiment of the present invention includes a tick octopamine receptor protein encoded by a nucleic acid molecule that hybridizes under conditions comprising, (a) hybridizing in a solution comprising 1×SSC in the absence of nucleic acid helix destabilizing compounds, at a temperature of 37° C. and (b) washing in a solution comprising 1×SSC in the absence of nucleic acid helix destabilizing compounds, at a temperature of 66.8° C., to an isolated nucleic acid molecule selected from the group consisting of SEQ ID NO:32, SEQ ID NO:35, SEQ ID NO:38 and SEQ ID NO:41.

Another preferred flea octopamine receptor protein of the present invention includes a protein that is encoded by a nucleic acid molecule that is preferably at least 70%, preferably at least 80%, preferably at least 90% identical, preferably at least 92% identical, preferably at least 95% identical or preferably at least 98% identical to a nucleic acid molecule having the nucleic acid sequence SEQ ID NO:1, SEQ ID NO:3, SEQ ID NO:6 and SEQ ID NO:11; also preferred are fragments (i.e. portions) of such proteins encoded by nucleic acid molecules that are at least 35 nucleotides. Percent identity as used herein is determined using the Needleman-Wunsch algorithm, available in the SeqLab software using default parameters.

Another preferred tick octopamine receptor protein of the present invention includes a protein that is encoded by a nucleic acid molecule that is preferably at least 70%, preferably at least 80%, preferably at least 90% identical, preferably at least 92% identical, preferably at least 95% identical or preferably at least 98% identical to a nucleic acid molecule having the nucleic acid sequence SEQ ID NO:30, SEQ ID NO:33, SEQ ID NO:36 and SEQ ID NO:39; also preferred are fragments (i.e. portions) of such proteins encoded by nucleic acid molecules that are at least 50 nucleotides. Percent identity as used herein is determined using the Needleman-Wunsch algorithm, available in the SeqLab software using default parameters.

Additional preferred flea octopamine receptor proteins of the present invention include proteins having the amino acid sequence SEQ ID NO:4, SEQ ID NO:7 and SEQ ID NO:12, and proteins comprising homologues of a protein having the amino acid sequence SEQ ID NO:4, SEQ ID NO:7 and SEQ ID NO:12, wherein such a homologue comprises at least one epitope that elicits an immune response against a protein having an amino acid sequence SEQ ID NO:4, SEQ ID NO:7 and SEQ ID NO:12. Likewise, also preferred are proteins encoded by nucleic acid molecules comprising nucleic acid sequence SEQ ID NO: 1, SEQ ID NO:3, SEQ ID NO:6 and SEQ ID NO:11.

Additional preferred tick octopamine receptor proteins of the present invention include proteins having the amino acid sequence SEQ ID NO:31, SEQ ID NO:34, SEQ ID NO:37 and SEQ ID NO:40, and proteins comprising homologues of a protein having the amino acid sequence SEQ ID NO:31, SEQ ID NO:34, SEQ ID NO:37 and SEQ ID NO:40, wherein such a homologue comprises at least one epitope that elicits an immune response against a protein having an amino acid sequence SEQ ID NO:31, SEQ ID NO:34, SEQ ID NO:37 and SEQ ID NO:40. Likewise, also preferred are proteins encoded by nucleic acid molecules comprising nucleic acid sequence SEQ ID NO:30, SEQ ID NO:33, SEQ ID NO:36 and SEQ ID NO:39

A preferred isolated flea octopamine receptor protein of the present invention is a protein encoded by at least one of the following nucleic acid molecules: $nCfOCR_{111}$, $nCfOCR_{2061}$, $nCfOCR_{868}$, and $nCfOCR_{2136}$, or allelic variants of any of these nucleic acid molecules and a preferred isolated tick octopamine receptor protein of the present invention is a protein encoded by at least one of the following nucleic acid molecules: $nRsOCR_{102}$, $nRsOCR_{499}$, $nRsOCR_{286}$, and $nRsOCR_{1443}$, or allelic variants of any of these nucleic acid molecules. Also preferred is an isolated protein encoded by a nucleic acid molecule having nucleic acid sequence SEQ ID NO:1, SEQ ID NO:3, SEQ ID NO:6, SEQ ID NO:11, SEQ ID NO:30, SEQ ID NO:33, SEQ ID NO:36 and SEQ ID NO:39; or a protein encoded by an allelic variant of any of these listed nucleic acid molecules.

Preferred octopamine receptor proteins of the present invention include proteins having amino acid sequences that are at least 70%, preferably 80%, preferably 90%, preferably 95%, preferably at least 98%, preferably at least 99%, or preferably 100% identical to amino acid sequence SEQ ID NO:4, SEQ ID NO:7, SEQ ID NO:12, SEQ ID NO:31, SEQ ID NO:34, SEQ ID NO:37 and SEQ ID NO:40; and proteins encoded by allelic variants of nucleic acid molecules encoding octopamine receptor proteins having amino acid sequences SEQ ID NO:4, SEQ ID NO:7, SEQ ID NO:12, SEQ ID NO:31, SEQ ID NO:34, SEQ ID NO:37 and SEQ ID NO:40.

Preferred flea octopamine receptor proteins of the present invention include proteins selected from the group consisting of (a) a protein comprising an amino acid sequence selected from the group consisting of SEQ ID NO:4, SEQ ID NO:7 and SEQ ID NO:12; and (b) a protein comprising an at least 40 contiguous amino acid portion identical in sequence to an at least 40 contiguous amino acid portion of an amino acid sequence of (a).

Preferred tick octopamine receptor proteins of the present invention include proteins selected from the group consisting of (a) a protein comprising an amino acid sequence selected from the group consisting of SEQ ID NO:31, SEQ ID NO:34, SEQ ID NO:37 and SEQ ID NO:40; and (b) a protein comprising an at least 20 contiguous amino acid portion identical in sequence to an at least 20 contiguous amino acid portion of an amino acid sequence of (a).

In one embodiment of the present invention, octopamine receptor proteins comprise amino acid sequence SEQ ID NO:4, SEQ ID NO:7, SEQ ID NO:12, SEQ ID NO:31, SEQ ID NO:34, SEQ ID NO:37 and SEQ ID NO:40 (including, but not limited to, the proteins consisting of amino acid sequence SEQ ID NO:4, SEQ ID NO:7, SEQ ID NO:12, SEQ ID NO:31, SEQ ID NO:34, SEQ ID NO:37 and SEQ ID NO:40, fusion proteins and multivalent proteins), and proteins encoded by allelic variants of nucleic acid molecules encoding proteins having amino acid sequence SEQ ID NO:4, SEQ ID NO:7, SEQ ID NO:12, SEQ ID NO:31, SEQ ID NO:34, SEQ ID NO:37 and SEQ ID NO:40.

In one embodiment, a preferred flea octopamine receptor protein comprises an amino acid sequence of at least 35 amino acids, preferably at least 50 amino acids, preferably at least 100 amino acids, preferably at least 125 amino acids, preferably at least 150 amino acids, preferably at least 175 amino acids, preferably at least 180 amino acids, preferably at least 190 amino acids, preferably at least 200 amino acids, preferably at least 225 amino acids, preferably at least 250 amino acids, preferably at least 275 amino acids, preferably at least 300 amino acids, preferably at least 350 amino acids, preferably at least 400 amino acids, preferably at least 450 amino acids, preferably at least 500 amino acids, preferably at least 550 amino acids, preferably at least 600 amino acids, preferably at least 650 amino acids, or preferably at least 690 amino acids.

In one embodiment, a preferred tick octopamine receptor protein comprises an amino acid sequence of at least 30 amino acids, preferably at least 35 amino acids, preferably at least 75 amino acids, preferably at least 95 amino acids, preferably at least 150 amino acids, preferably at least 200 amino acids, preferably at least 300 amino acids, preferably at least 400 amino acids, preferably at least 450 amino acids, preferably at least 475 amino acids, or preferably at least 480 amino acids.

In another embodiment, preferred flea and tick octopamine receptor proteins comprise full-length proteins, i.e., proteins encoded by full-length coding regions, or post-translationally modified proteins thereof such as mature proteins from which initiating methionine and/or signal sequences or "pro" sequences have been removed.

Also preferred are flea octopamine receptor proteins encoded by nucleic acid molecules having nucleic acid sequences comprising at least a portion of SEQ ID NO:1, SEQ ID NO:3, SEQ ID NO:6 and SEQ ID NO:11, as well as allelic variants of these nucleic acid molecules. A portion of such flea octopamine receptor nucleic acid molecule is preferably at least 35 nucleotides in length.

Also preferred are tick octopamine receptor proteins encoded by nucleic acid molecules having nucleic acid sequences comprising at least a portion of SEQ ID NO:30, SEQ ID NO:33, SEQ ID NO:36 and SEQ ID NO:39, as well as allelic variants of these nucleic acid molecules. A portion of such tick octopamine receptor nucleic acid molecule is preferably at least 50 nucleotides in length.

In another embodiment, a preferred flea octopamine receptor protein of the present invention is encoded by a nucleic acid molecule comprising at least 30 nucleotides, preferably at least 50 nucleotides, preferably at least 75 nucleotides, preferably at least 100 nucleotides, preferably at least 125 nucleotides, preferably at least 150 nucleotides, preferably at least 175 nucleotides, preferably at least 200 nucleotides, preferably at least 250 nucleotides, preferably at least 350 nucleotides, preferably at least 450 nucleotides, preferably at least 550 nucleotides, preferably at least 650 nucleotides, preferably at least 750 nucleotides, preferably at least 1000 nucleotides, preferably at least 1500 nucleotides, preferably at least 1750 nucleotides, preferably at least 2000 nucleotides or preferably at least 2050 nucleotides in length that bind octopamine. Preferred flea octopamine receptor proteins of the present invention are encoded by nucleic acid molecules comprising apparently full-length flea octopamine receptor coding region, i.e., nucleic acid molecules encoding an apparently full-length flea octopamine receptor protein, or extracellular domain.

In another embodiment, a preferred tick octopamine receptor protein of the present invention is encoded by a nucleic acid molecule comprising at least 30 nucleotides, preferably at least 50 nucleotides, preferably at least 75 nucleotides, preferably at least 100 nucleotides, preferably at least 150 nucleotides, preferably at least 250 nucleotides, preferably at least 500 nucleotides, preferably at least 750 nucleotides, preferably at least 1000 nucleotides, preferably at least 1250 nucleotides, preferably at least 1400 nucleotides or preferably at least 1440 nucleotides in length that bind octopamine. Preferred tick octopamine receptor proteins of the present invention are encoded by nucleic acid molecules comprising apparently full-length tick octopamine receptor coding region, i.e., nucleic acid molecules encoding an apparently full-length tick octopamine receptor protein, or extracellular domain.

Preferred flea or tick octopamine receptor proteins of the present invention can be used to develop inhibitors that, when administered to an animal in an effective manner, are capable of protecting that animal from flea or tick infestation. In accordance with the present invention, the ability of an inhibitor of the present invention to protect an animal from flea or tick infestation refers to the ability of that inhibitor to, for example, treat, ameliorate and/or prevent infestation caused by fleas or ticks. In particular, the phrase "to protect an animal from flea or tick infestation" refers to reducing the potential for flea or tick population expansion on and around the animal (i.e., reducing the flea or tick burden). Preferably, the flea or tick population size is decreased, optimally to an extent that the animal is no longer bothered by fleas or ticks. A host animal, as used herein, is an animal from which fleas or ticks can feed by attaching to and feeding through the skin of the animal. Fleas, ticks, and other ectoparasites, can live on a host animal for an extended period of time or can attach temporarily to an animal in order to feed. At any given time, a certain percentage of a flea or tick population can be on a host animal whereas the remainder can be in the environment of the animal. Such an environment can include not only adult fleas or ticks, but also flea or tick eggs and/or flea or tick larvae. The environment can be of any size such that fleas or ticks in the environment are able to jump onto and off of a host animal. For example, the environment of an animal can include plants, such as crops, from which fleas or ticks infest an animal. As such, it is desirable not only to reduce the flea or tick burden on an animal per se, but also to reduce the flea or tick burden in the environment of the animal.

Suitable fleas to target include any flea that is essentially incapable of causing disease in an animal administered an inhibitor of the present invention. As such, fleas to target include any flea that produces a protein that can be targeted by an inhibitory compound that inhibits a flea flea octopamine receptor protein function, thereby resulting in the decreased ability of the parasite to cause disease in an animal. Preferred fleas to target include fleas of the following genera: *Ctenocephalides, Cyopsyllus, Diamanus (Oropsylla), Echidnophaga, Nosopsyllus, Pulex, Tunga,* and *Xenopsylla*, with those of the species *Ctenocephalides canis, Ctenocephalides felis, Diamanus montanus, Echidnophaga gallinacea, Nosopsyllus faciatus, Pulex irritans, Pulex simulans, Tunga penetrans* and *Xenopsylla cheopis* being more preferred, with *C. felis* being even more preferred. Such fleas are also preferred for the isolation of proteins or nucleic acid molecules of the present invention.

Suitable ticks to target include any tick that is essentially incapable of causing disease in an animal administered an inhibitor of the present invention. As such, ticks to target include any tick that produces a protein that can be targeted by an inhibitory compound that inhibits a tick tick octopamine receptor protein function, thereby resulting in the decreased ability of the parasite to cause disease in an animal. Preferred ticks to target include ticks of the following genera: *Amblyomma, Dermacentor, Ixodes* and *Rhipicephalus*, with those of the species *Amblyomma americanum, Amblyomma maculatum, Dermacentor abipictus, Dermacentor andersoni, Dermacentor variabilis, Ixodes scapularis* and *Rhipicephalus sanguineus* being more preferred. Such ticks are also preferred for the isolation of proteins or nucleic acid molecules of the present invention.

Another embodiment of the present invention is an isolated nucleic acid molecule comprising a flea or tick octopamine receptor nucleic acid molecule, i.e. a nucleic acid molecule that can be isolated from a flea or tick cDNA library. The identifying characteristics of such nucleic acid molecules are heretofore described. A nucleic acid molecule of the present invention can include an isolated natural flea or tick octopamine receptor gene or a homologue thereof the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of a flea or tick octopamine receptor nucleic acid molecule of the present invention is from 12 to 18 nucleotides in length.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. Isolated flea or tick octopamine receptor nucleic acid molecules of the present invention, or homologues thereof, can be isolated from a natural source or produced using recombinant DNA technology (e.g., polymerase chain reaction (PCR) amplification or cloning) or chemical synthesis. Isolated flea or tick octopamine receptor nucleic acid molecules, and homologues thereof, can include, for example, natural allelic variants and nucleic acid molecules modified by nucleotide insertions, deletions, substitutions, and/or inversions in a manner such that the modifications do not substantially interfere with the nucleic acid molecule's ability to encode a flea or tick octopamine receptor protein of the present invention.

A flea or tick octopamine receptor nucleic acid molecule homologue can be produced using a number of methods known to those skilled in the art, see, for example, Sambrook et al., ibid., which is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologues can be selected by hybridization with flea or tick octopamine receptor nucleic acid molecules or by screening the function of a protein encoded by the nucleic acid molecule (e.g., ability to elicit an immune response against at least one epitope of a flea or tick octopamine receptor protein or to effect flea or tick octopamine receptor activity).

An isolated flea or tick octopamine receptor nucleic acid molecule of the present invention can include a nucleic acid sequence that encodes at least one flea or tick octopamine receptor protein of the present invention respectively, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a flea or tick octopamine receptor protein.

In one embodiment of the present invention, a preferred flea or tick octopamine receptor nucleic acid molecule includes an isolated nucleic acid molecule that hybridizes under conditions that preferably allow less than or equal to 30% base pair mismatch, preferably under conditions that allow less than or equal to 20% base pair mismatch, preferably under conditions that allow less than or equal to 10% base pair mismatch, preferably under conditions that allow less than or equal to 8% base pair mismatch, preferably under conditions that allow less than or equal to 5% base pair mismatch or preferably under conditions that allow less than or equal to 2% base pair mismatch with a nucleic acid molecule selected from the group consisting of SEQ ID NO:1, SEQ ID NO:2, SEQ ID NO:3, SEQ ID NO:5, SEQ ID NO:6, SEQ ID NO:8, SEQ ID NO:11, SEQ ID NO:13, SEQ ID NO:30, SEQ ID NO:32, SEQ ID NO:33, SEQ ID NO:35, SEQ ID NO:36, SEQ ID NO:38, SEQ ID NO:39, and SEQ ID NO:41.

One embodiment of the present invention includes a flea octopamine receptor nucleic acid molecule, wherein said nucleic acid molecule hybridizes under conditions comprising, (a) hybridizing in solution comprising 1×SSC in the absence of nucleic acid helix destabilizing compounds, at a temperature of 37° C. and (b) washing in a solution comprising 1×SSC in the absence of nucleic acid helix destabilizing compounds, at a temperature of 74.6° C., to an isolated nucleic acid molecule selected from the group consisting of SEQ ID NO:1, SEQ ID NO:2, SEQ ID NO:3, SEQ ID NO:5, SEQ ID NO:6, SEQ ID NO:8, SEQ ID NO:11 and SEQ ID NO:13.

One embodiment of the present invention includes a tick octopamine receptor nucleic acid molecule, wherein said nucleic acid molecule hybridizes under conditions comprising, (a) hybridizing in solution comprising 1×SSC in the absence of nucleic acid helix destabilizing compounds, at a temperature of 37° C. and (b) washing in a solution comprising 1×SSC in the absence of nucleic acid helix destabilizing compounds, at a temperature of 74.6° C., to an isolated nucleic acid molecule selected from the group consisting of SEQ ID NO:30, SEQ ID NO:32, SEQ ID NO:33, SEQ ID NO:35, SEQ ID NO:36, SEQ ID NO:38, SEQ ID NO:39, and SEQ ID NO:41.

Additional preferred flea octopamine receptor nucleic acid molecules of the present invention include nucleic acid molecules comprising a nucleic acid sequence at least 35 nucleotides in length that is preferably at least 70%, preferably at least 80%, preferably at least 90%, preferably at least 92%, preferably at least 95%, or preferably at least 98% identical to a nucleic acid sequence selected from the group consisting of SEQ ID NO:1, SEQ ID NO:3, SEQ ID NO:6 and SEQ ID NO:11 and encodes a protein that binds octopamine.

Additional preferred tick octopamine receptor nucleic acid molecules of the present invention include nucleic acid molecules comprising a nucleic acid sequence at least 50 nucleotides in length that is preferably at least 70%, preferably at least 80%, preferably at least 90%, preferably at least 92%, preferably at least 95%, or preferably at least 98% identical to a nucleic acid sequence selected from the group consisting of SEQ ID NO:30, SEQ ID NO:33, SEQ ID NO:36 and SEQ ID NO:39 and encodes a protein that binds octopamine.

One preferred nucleic acid molecule of the present invention includes at least a portion of nucleic acid sequence SEQ ID NO:1, SEQ ID NO:2, SEQ ID NO:3, SEQ ID NO:5, SEQ ID NO:6, SEQ ID NO:8, SEQ ID NO:11, SEQ ID NO:13, SEQ ID NO:30, SEQ ID NO:32, SEQ ID NO:33, SEQ ID NO:35, SEQ ID NO:36, SEQ ID NO:38, SEQ ID NO:39, and SEQ ID NO:41, as well as allelic variants of nucleic acid molecules having these nucleic acid sequences and homologues of nucleic acid molecules having these nucleic acid sequences; preferably such a homologue encodes or is complementary to a nucleic acid molecule that encodes at least one epitope that elicits an immune response against a protein having an amino acid sequence SEQ ID NO:1, SEQ ID NO:2, SEQ ID NO:3, SEQ ID NO:5, SEQ ID NO:6, SEQ ID NO:8, SEQ ID NO:11, SEQ ID NO:13, SEQ ID NO:30, SEQ ID NO:32, SEQ ID NO:33, SEQ ID NO:35, SEQ ID NO:36, SEQ ID NO:38, SEQ ID NO:39, and SEQ ID NO:41. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

One embodiment of the present invention is a nucleic acid molecule comprising an isolated nucleic acid molecule having a nucleic acid sequence selected from the group consisting of: (a) a nucleic acid sequence selected from the group consisting of SEQ ID NO:1, SEQ ID NO:2, SEQ ID NO:3, SEQ ID NO:5, SEQ ID NO:6, SEQ ID NO:8, SEQ ID NO:11, SEQ ID NO:13, SEQ ID NO:30, SEQ ID NO:32, SEQ ID NO:33, SEQ ID NO:35, SEQ ID NO:36, SEQ ID NO:38, SEQ ID NO:39, and SEQ ID NO:41; (b) a nucleic acid molecule having an at least 35 contiguous nucleotide portion identical in sequence to an at least 35 contiguous nucleotide portion of a nucleic acid sequence selected from the group consisting of SEQ ID NO:1, SEQ ID NO:2, SEQ ID NO:3, SEQ ID NO:5, SEQ ID NO:6, SEQ ID NO:8, SEQ ID NO:11, and SEQ ID NO:13; and (c) a nucleic acid molecule having an at least 50 contiguous nucleotide portion identical in sequence to an at least 50 contiguous nucleotide portion of a nucleic acid sequence selected from the group consisting of SEQ ID NO:30, SEQ ID NO:32, SEQ ID NO:33, SEQ ID NO:35, SEQ ID NO:36, SEQ ID NO:38, SEQ ID NO:39, and SEQ ID NO:41.

In one embodiment, an octopamine receptor nucleic acid molecule of the present invention encodes a protein having an amino acid sequence that is at least 70%, preferably at least 80%, preferably at least 90%, preferably at least 95%, preferably at least 98%, preferably at least 99%, or preferably at least 100% identical to SEQ ID NO:4, SEQ ID NO:7, SEQ ID NO:12, SEQ ID NO:31, SEQ ID NO:34, SEQ ID NO:37 and SEQ ID NO:40. The present invention also includes an octopamine receptor nucleic acid molecule encoding a protein having at least a portion of SEQ ID NO:4, SEQ ID NO:7, SEQ ID NO:12, SEQ ID NO:31, SEQ ID NO:34, SEQ ID NO:37 and SEQ ID NO:40, as well as allelic variants of a nucleic acid molecule encoding a protein having these sequences, including nucleic acid molecules that have been modified to accommodate codon usage properties of the cells in which such nucleic acid molecules are to be expressed.

In another embodiment, a preferred flea octopamine receptor nucleic acid molecule of the present invention comprises a nucleic acid molecule comprising at least 35 nucleotides, preferably at least 40 nucleotides, preferably at least 45 nucleotides, preferably at least 50 nucleotides, preferably at least 75 nucleotides, preferably at least 100 nucleotides, preferably at least 125 nucleotides, preferably at least 150 nucleotides, preferably at least 175 nucleotides, preferably at least 200 nucleotides, preferably at least 250 nucleotides, preferably at least 350 nucleotides, preferably at least 400 nucleotides, preferably at least 450 nucleotides, preferably at least 500 nucleotides, preferably at least 550 nucleotides, preferably at least 600 nucleotides, preferably at least 650 nucleotides, preferably at least 700 nucleotides, preferably at least 750 nucleotides, preferably at least 1000 nucleotides, preferably at least 1500 nucleotides, preferably at least 1750 nucleotides, preferably at least 2000 nucleotides or preferably at least 2050 nucleotides in length and encodes a protein that binds octopamine.

In another embodiment, a preferred tick octopamine receptor nucleic acid molecule of the present invention comprises a nucleic acid molecule comprising at least 30 nucleotides, preferably at least 50 nucleotides, preferably at least 75 nucleotides, preferably at least 100 nucleotides, preferably at least 150 nucleotides, preferably at least 250 nucleotides, preferably at least 500 nucleotides, preferably at least 750 nucleotides, preferably at least 1000 nucleotides, preferably at least 1250 nucleotides, preferably at least 1400 nucleotides or preferably at least 1440 nucleotides in length and encodes a protein that binds octopamine.

In another embodiment, a preferred flea octopamine receptor nucleic acid molecule encodes a protein comprising at least 180 amino acids, preferably at least 200 amino acids, preferably at least 225 amino acids, preferably at least 250 amino acids, preferably at least 300 amino acids, preferably at least 350 amino acids, preferably at least 400 amino acids, preferably at least 450 amino acids, preferably at least 500 amino acids, preferably at least 550 amino acids, preferably at least 600 amino acids, preferably at least 650 amino acids, or preferably at least 690 amino acids.

In another embodiment, a preferred tick octopamine receptor nucleic acid molecule encodes a protein comprising at least 30 amino acids, preferably at least 35 amino acids, preferably at least 75 amino acids, preferably at least 95 amino acids, preferably at least 150 amino acids, preferably at least 200 amino acids, preferably at least 300 amino acids, preferably at least 400 amino acids, preferably at least 450 amino acids, preferably at least 475 amino acids, or preferably at least 480 amino acids.

In another embodiment, a preferred flea or tick octopamine receptor nucleic acid molecule of the present invention comprises an apparently full-length flea or tick octopamine receptor coding region, i.e., the preferred nucleic acid molecule encodes an apparently full-length flea or tick octopamine receptor protein, respectively, or a post-translationally modified protein thereof. In one embodiment, a preferred flea or tick octopamine receptor nucleic acid molecule of the present invention encodes a mature protein or extracellular domain.

In another embodiment, a preferred octopamine receptor nucleic acid molecule of the present invention comprises a nucleic acid molecule comprising SEQ ID NO:1, SEQ ID NO:2, SEQ ID NO:3, SEQ ID NO:5, SEQ ID NO:6, SEQ ID NO:8, SEQ ID NO:11, SEQ ID NO:13, SEQ ID NO:30, SEQ ID NO:32, SEQ ID NO:33, SEQ ID NO:35, SEQ ID NO:36, SEQ ID NO:38, SEQ ID NO:39, and SEQ ID NO:41, or a fragment thereof.

A flea octopamine receptor nucleic acid molecule of the present invention preferably comprises at least 35 nucleotides, preferably at least 40 nucleotides, preferably at least 45 nucleotides, preferably at least 50 nucleotides, preferably at least 75 nucleotides, preferably at least 100 nucleotides, preferably at least 125 nucleotides, preferably at least 150 nucleotides, preferably at least 175 nucleotides, preferably at least 200 nucleotides, preferably at least 250 nucleotides, preferably at least 350 nucleotides, preferably at least 400 nucleotides, preferably at least 450 nucleotides, preferably at least 500 nucleotides, preferably at least 550 nucleotides, preferably at least 600 nucleotides, preferably at least 650 nucleotides, preferably at least 700 nucleotides, preferably at least 750 nucleotides, preferably at least 1000 nucleotides, preferably at least 1500 nucleotides, preferably at least 1750 nucleotides or preferably at least 2000 nucleotides identical in sequence to a corresponding contiguous sequence selected from the group consisting of SEQ ID NO:1, SEQ ID NO:2, SEQ ID NO:3, SEQ ID NO:5, SEQ ID NO:6, SEQ ID NO:8, SEQ ID NO:11 and SEQ ID NO:13.

A tick octopamine receptor nucleic acid molecule of the present invention preferably comprises at least 30 nucleotides, preferably at least 50 nucleotides, preferably at least 75 nucleotides, preferably at least 100 nucleotides, preferably at least 150 nucleotides, preferably at least 250 nucleotides, preferably at least 500 nucleotides, preferably at least 750 nucleotides, preferably at least 1000 nucleotides, preferably at least 1250 nucleotides, preferably at least 1400 nucleotides or preferably at least 1440 nucleotides identical in sequence to a corresponding contiguous sequence selected from the group consisting of SEQ ID NO:30, SEQ ID NO:32, SEQ ID NO:33, SEQ ID NO:35, SEQ ID NO:36, SEQ ID NO:38, SEQ ID NO:39, and SEQ ID NO:41.

The phrase, a nucleic acid molecule comprising at least "x" contiguous, or consecutive nucleotides identical in sequence to at least "x" contiguous, or consecutive nucleotides of a nucleic acid molecule selected from the group consisting of SEQ ID NO:"y", refers to an "x"-nucleotide in length nucleic acid molecule that is identical in sequence to an "x"-nucleotide portion of SEQ ID NO:"y", as well as to nucleic acid molecules that are longer in length than "x". The additional length may be in the form of nucleotides that extend from either the 5' or the 3' end(s) of the contiguous identical "x"-nucleotide portion. The 5' and/or 3' extensions can include one or more extensions that have no identity to a molecule of the present invention, as well as extensions that show similarity or identity to cited nucleic acids sequences or portions thereof.

Knowing the nucleic acid sequences of certain flea or tick octopamine receptor nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other flea or tick octopamine receptor nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include cDNA libraries as well as genomic DNA libraries. Similarly, preferred DNA sources to screen or from which to amplify nucleic acid molecules include cDNA and genomic DNA. Techniques to clone and amplify genes are disclosed, for example, in Sambrook et al., *ibid.*

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of flea or tick octopamine receptor nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences that control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those that function in bacterial, yeast, or insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, *Pichia* alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with fleas and ticks, such as *C. felis* and *R. sanguineus* transcription control sequences. Suitable and preferred nucleic acid molecules to include in recombinant vectors of the present invention are as disclosed herein.

Recombinant molecules of the present invention may also (a) contain secretory signals (i.e., signal segment nucleic acid sequences) to enable an expressed flea or tick octopamine receptor protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include flea or tick octopamine receptor nucleic acid molecules disclosed herein.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing flea or tick octopamine receptor proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast insect and mammalian cells. More preferred host cells include *Drosophila melanogaster* S2 cells, *Salmonella, Escherichia, Bacillus, Caulobacter, Listeria, Saccharomyces, Pichia, Spodoptera, Mycobacteria, Trichoplusia*, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1 $_\chi$3987 and SR-11 $_\chi$4072; *Caulobacter; Pichia; Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK[31] cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein. The phrase operatively linked refers to insertion of a nucleic acid molecule into an expression vector in a manner such that the molecule is able to be expressed when transformed into a host cell.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including flea or tick octopamine receptor nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated flea or tick octopamine receptor proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a flea or tick octopamine receptor protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a flea or tick octopamine receptor protein of the present invention or a mimetope thereof (e.g., anti-flea or anti-tick octopamine receptor antibodies). As used herein, the term "selectively binds to" a protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., *ibid.*, and Harlow, et al., 1988, *Antibodies, a Laboratory Manual*, Cold Spring Harbor Labs Press; Harlow et al., *ibid.*, is incorporated by reference herein in its entirety. An anti-flea or anti-tick octopamine receptor antibody of the present invention preferably selectively binds to a flea or tick octopamine receptor protein, respectively, in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

One embodiment of the present invention is a therapeutic composition that, when administered to an animal susceptible to flea or tick infestation, is capable of protecting that animal from flea or tick infestation. Therapeutic compositions of the present invention include at least one of the following protective molecules: an isolated flea or tick octopamine receptor protein; a mimetope of an isolated flea or tick octopamine receptor protein; an isolated flea or tick octopamine receptor nucleic acid molecule; and/or a compound derived from said isolated flea or tick octopamine receptor protein that inhibits flea or tick octopamine receptor protein activity, an anti-flea or anti-tick octopamine receptor antibody, and/or a compound that inhibits flea or tick octopamine receptor activity. A therapeutic composition of the present invention can further comprise a component selected from the group of an excipient, a carrier, and/or an adjuvant; these components are described further herein. As used herein, a protective molecule or protective compound refers to a compound that, when administered to an animal in an effective manner, is able to treat, ameliorate, and/or prevent flea or tick infestation.

Preferred fleas and ticks to target are heretofore disclosed. One example of a protective molecule is a vaccine or therapy, such as, but not limited to, a naked nucleic acid vaccine or therapy, a recombinant virus vaccine or therapy, a recombinant cell vaccine or therapy, and a recombinant protein vaccine or therapy. Another example of a protective molecule is a compound that inhibits flea or octopamine receptor protein activity, such as an isolated antibody that selectively binds to a flea or tick octopamine receptor protein, a substrate analog of a flea or tick octopamine receptor protein, anti-sense-, triplex formation-, ribozyme-, and/or RNA drug-based compounds, or other inorganic or organic molecules that inhibit flea or tick octopamine receptor protein activity. Inhibiting flea or tick octopamine receptor protein activity can refer to the ability of a compound to reduce the activity of flea or tick octopamine receptor proteins. Inhibiting flea or tick octopamine receptor protein activity can also refer to the ability of a compound to reduce the amount of flea or tick octopamine receptor protein in a flea or tick.

Another embodiment of the present invention includes a method to reduce flea or tick infestation in an animal susceptible to tick infestation. Such a method includes the step of administering to the animal a therapeutic molecule comprising a protective compound selected from the group consisting of (a) an isolated flea or tick octopamine receptor protein; (b) a mimetope of an isolated flea or tick octopamine receptor protein; (c) an isolated flea or tick octopamine receptor nucleic acid molecule; and (d) a compound derived from an isolated flea or tick octopamine receptor protein that inhibits flea or tick octopamine receptor protein activity.

As used herein, the term derived, or the term derived from, refers to a peptide, antibody, mimetope, nucleic acid molecule, or other compound that was obtained directly or indirectly from a flea or tick octopamine receptor protein or nucleic acid molecule of the present invention, e.g. a part of a protein or nucleic acid molecule or produced using a protein or nucleic acid molecule of the present invention. Methods to obtain derivatives from a flea or tick octopamine receptor molecule of the present invention are known in the art, and as such include, but are not limited to molecular modeling of flea or tick octopamine receptor proteins to determine active sites, and predicting from these active sites smaller fragments and/or mimetopes that retain and/or mimic these active sites, thereby inhibiting flea or tick octopamine receptor protein activity. Other inhibitors of flea or tick octopamine receptor activity can also be obtained in a variety of ways, including but not limited to screening of peptide or small chemical compound libraries against flea or tick octopamine receptor proteins of the present invention; and screening of polyclonal or monoclonal antibodies to find antibodies that specifically bind flea or tick octopamine receptor proteins of the present invention.

A flea or tick octopamine receptor protein inhibitor of the present invention (i.e. an inhibitor of a flea or tick octopamine receptor protein) is identified by its ability to mimic, bind to, modify, or otherwise interact with, a flea or tick octopamine receptor protein, thereby inhibiting the activity of a natural flea or tick octopamine receptor protein. Suitable inhibitors of flea or tick octopamine receptor protein activity are compounds that can inhibit flea or tick octopamine receptor protein activity in at least one of a variety of ways: (a) by binding to or otherwise interacting with or otherwise modifying flea or tick octopamine receptor protein sites; (b) by binding to or otherwise interacting with or otherwise modifying flea or tick octopamine receptor protein active site(s); (c) by binding to the flea or tick octopamine receptor protein and thus reducing the availability of the flea or tick octopamine receptor protein in solution; (d) by mimicking a flea or tick octopamine receptor protein; and (e) by interacting with other regions of the flea or tick octopamine receptor protein to inhibit flea or tick octopamine receptor protein activity, for example, by allosteric interaction.

Flea or tick octopamine receptor protein inhibitors can be used directly as compounds in compositions of the present invention to treat animals as long as such compounds are not harmful to host animals being treated. Preferred flea or tick octopamine receptor protein inhibitors of the present invention include, but are not limited to, flea or tick octopamine receptor protein substrate analogs, and other molecules that bind to a flea or tick octopamine receptor protein (e.g., to an allosteric site) in such a manner that the activity of the flea or tick octopamine receptor protein is inhibited. A flea or tick octopamine receptor protein substrate analog refers to a compound that interacts with (e.g., binds to, associates with, modifies) the active site of a flea or tick octopamine receptor protein. A preferred flea or tick octopamine receptor protein substrate analog inhibits flea or tick octopamine receptor protein activity. Flea or tick octopamine receptor protein substrate analogs can be of any inorganic or organic composition. Flea or tick octopamine receptor protein substrate analogs can be, but need not be, structurally similar to a flea or tick octopamine receptor protein natural substrate as long as they can interact with the active site of that flea or tick octopamine receptor protein. Flea or tick octopamine receptor protein substrate analogs can be designed using computer-generated structures of flea or tick octopamine receptor proteins of the present invention or computer structures of flea or tick octopamine receptor protein's natural substrates. Preferred sites to model include one or more of the active sites of flea or tick octopamine receptor proteins. Substrate analogs can also be obtained by generating random samples of molecules, such as oligonucleotides, peptides, peptidomimetic compounds, or other inorganic or organic molecules, and screening such samples for their ability to interfere with interaction between flea or tick octopamine receptor proteins and their substrates, e.g. by affinity chromatography techniques. A preferred flea or tick octopamine receptor protein substrate analog is a flea or tick octopamine receptor protein mimetic compound, i.e., a compound that is structurally and/or functionally similar to a natural substrate of a flea or tick octopamine receptor protein of the present invention, particularly to the region of the substrate that interacts with the flea or tick octopamine receptor protein active site, but that inhibits flea or tick octopamine receptor protein activity upon interacting with the flea or tick octopamine receptor protein active site.

The present invention also includes a therapeutic composition comprising at least one protective molecule of the present invention in combination with at least one additional compound protective against one or more infectious agents and/or infestation by one or more ectoparasites.

In one embodiment, a therapeutic composition of the present invention can be used to protect an animal from flea or tick infestation by administering such composition to a flea or tick in order to prevent infestation. Such administration to the flea or tick and/or animal could be oral, or by application to the animal's body surface (e.g. topical spot-on, or spraying onto the animal), or by application to the environment (e.g., spraying). Examples of such compositions include, but are not limited to, transgenic vectors capable of producing at least one therapeutic composition of the present invention. In another embodiment a flea or tick can ingest therapeutic compositions, or products thereof present on the surface of or in the blood of a host animal that has been administered a therapeutic composition of the present invention.

In accordance with the present invention, a host animal (i.e., an animal that is or is capable of being infested with fleas or ticks) is treated by administering to the animal a therapeutic composition of the present invention in such a manner that the composition itself (e.g., a flea or tick octopamine receptor protein inhibitor, a octopamine receptor protein synthesis suppressor (i.e., a compound that decreases the production or half-life of a octopamine receptor protein in fleas or ticks), a flea or tick octopamine receptor protein mimetope, or a anti-flea or tick octopamine receptor antibody) or a product generated by the animal in response to administration of the composition (e.g., antibodies produced in response to administration of a flea or tick octopamine receptor protein or nucleic acid molecule, or conversion of an inactive inhibitor "prodrug" to an active flea or tick octopamine receptor protein inhibitor) ultimately enters the flea or tick. A host animal is preferably treated in such a way that the compound or product thereof is present on the body surface of the animal or enters the blood stream of the animal. Fleas or ticks are then exposed to the composition or product when they feed from the animal. For example, flea or tick octopamine receptor protein inhibitors administered to an animal are administered in such a way that the inhibitors enter the blood stream of the animal, where they can be taken up by feeding fleas or ticks or are administered to the animal topically, where they can be taken up by contact with the treated animal.

In accordance with the present invention, reducing flea or tick octopamine receptor protein activity in a flea or tick can lead to a number of outcomes that reduce flea or tick burden on treated animals and their surrounding environments. Such outcomes include, but are not limited to, (a) reducing the viability of fleas or ticks that feed from the treated animal, (b) reducing the fecundity of female fleas or ticks that feed from the treated animal, (c) reducing the reproductive capacity of male fleas or ticks that feed from the treated animal, (d) reducing the viability of eggs laid by female fleas or ticks that feed from the treated animal, (e) altering the blood feeding behavior of fleas or ticks that feed from the treated animal (e.g., fleas or ticks take up less volume per feeding or feed less frequently), (f) reducing the viability of flea or tick larvae, for example due to the feeding of larvae from feces of fleas or ticks that feed from the treated animal, (g) altering the development of flea or tick larvae (e.g., by decreasing feeding behavior, inhibiting growth, inhibiting (e.g., slowing or blocking) molting, and/or otherwise inhibiting maturation to adults), and/or (h) altering or decreasing the ability of fleas or ticks and/or their larvae to digest a blood meal.

In order to protect an animal from flea or tick infestation, a therapeutic composition of the present invention is administered to the animal in an effective manner such that the composition is capable of protecting that animal from flea or tick infestation. Therapeutic compositions of the present invention can be administered to animals prior to infestation in order to prevent infestation (i.e., as a preventative vaccine) and/or can be administered to animals after infestation (i.e. as a therapy).

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability.

Examples of buffers include phosphate buffer, bicarbonate buffer and Tris buffer, while examples of preservatives include thimerosal, or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), Flt-3 ligand, granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and *Leishmania* elongation initiating factor (LEIF)); bacterial components (e.g., endotoxins, in particular superantigens, exotoxins and cell wall components); aluminum-based salts; calcium-based salts; silica; polynucleotides; toxoids; serum proteins; viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition. The therapeutic composition is preferably released over a period of time ranging from about 1 to about 12 months. A controlled release formulation of the present invention is capable of effecting a treatment preferably for at least 1 month, more preferably for at least 3 months, even more preferably for at least 6 months, even more preferably for at least 9 months, and even more preferably for at least 12 months.

The efficacy of a therapeutic composition of the present invention to protect an animal from flea or tick infestation can be tested in a variety of ways including, but not limited to challenge of the treated animal with the flea or tick to determine whether the treated animal is resistant to infestation. Challenge studies can include direct administration of flea or tick to the treated animal. In one embodiment, therapeutic compositions can be tested in animal models such as mice. Such techniques are known to those skilled in the art.

As discussed herein, one therapeutic composition of the present invention includes an inhibitor of flea or tick octopamine receptor protein activity, i.e., a compound capable of substantially interfering with the function of a flea or tick octopamine receptor protein. An inhibitor of flea or tick octopamine receptor protein activity, or function, can be identified using flea or tick octopamine receptor proteins of the present invention. A preferred inhibitor of flea or tick octopamine receptor protein function is a compound capable of substantially interfering with the function of a flea or tick octopamine receptor protein and which does not substantially interfere with the function of host animal octopamine receptor proteins. As used herein, a compound that does not substantially inhibit or interfere with host animal octopamine receptor proteins is one that, when administered to a host animal, the host animal shows no significant adverse effects attributable to the inhibition of octopamine receptor and which, when administered to an animal in an effective manner, is capable of protecting that animal from flea or tick infestation.

One embodiment of the present invention is a method to identify a compound capable of inhibiting flea or tick octopamine receptor protein activity. Such a method includes the steps of (a) contacting (e.g., combining, mixing) an isolated flea or tick octopamine receptor protein of the present invention, with a putative inhibitory compound under conditions in which, in the absence of the compound, the protein has flea or tick octopamine receptor protein activity, and (b) determining if the putative inhibitory compound inhibits the activity. Flea or tick octopamine receptor protein activity can be determined in a variety of ways known in the art, including but not limited to determining the ability of flea or tick octopamine receptor protein to bind to or otherwise interact with a substrate. Such conditions under which a flea or tick octopamine receptor protein has flea or tick octopamine receptor protein activity include conditions in which a flea or tick octopamine receptor protein has a correct three-dimensionally folded structure under physiologic conditions, i.e. physiologic pH, physiologic ionic concentrations, and physiologic temperatures, such as a native protein, a mature protein, a soluble protein, transfected cells or viruses. Accordingly, the correct three-dimensionally folded structure could be used to predict inhibitory compounds.

Putative inhibitory compounds to screen include antibodies (including fragments and mimetopes thereof), putative substrate analogs, and other, preferably small, organic or inorganic molecules. Methods to determine flea or tick octopamine receptor protein activity are known to those skilled in the art, see for example Han et al. 1996, Neuron 16:1127-1135.

A preferred method to identify a compound capable of inhibiting flea or tick octopamine receptor protein activity includes contacting an isolated flea or tick octopamine receptor protein of the present invention with a putative inhibitory compound under conditions in which, in the absence of the compound, the protein has flea or tick octopamine receptor protein activity; and determining if the putative inhibitory compound inhibits the activity.

A preferred method to identify a compound capable of inhibiting flea or tick octopamine receptor protein activity includes contacting a recombinant cell comprising an isolated flea or tick octopamine receptor protein of the present invention with a putative inhibitory compound under conditions in which, in the absence of the compound, the protein has flea or tick octopamine receptor protein activity; and determining if the putative inhibitory compound inhibits the activity.

Another embodiment of the present invention is an assay kit to identify an inhibitor of a flea or tick octopamine receptor protein of the present invention. This kit comprises an isolated flea or tick octopamine receptor protein of the present invention, and a means for determining inhibition of an activity of flea or tick octopamine receptor protein, where the means enables detection of inhibition. Detection of inhibition of a flea or tick octopamine receptor protein identifies a putative inhibitor to be an inhibitor of a flea or tick octopamine receptor protein. Means for determining inhibition of a flea or tick octopamine receptor protein include, for example, an assay system that detects binding of a putative inhibitor to a flea or tick octopamine receptor molecule, and an assay system that detects interference by a putative inhibitor of the ability of flea or tick octopamine receptor protein to bind octopamine. Means and methods are described herein and are known to those skilled in the art.

The following examples are provided for the purposes of illustration and are not intended to limit the scope of the present invention. The following examples include a number of recombinant DNA and protein chemistry techniques known to those skilled in the art; see, for example, Sambrook et al., *ibid*.

EXAMPLE 1

This example describes the preparation of flea genomic DNA and a flea head and nerve cord cDNA pool by Rapid Amplification of cDNA Ends (RACE pool).

Genomic DNA was isolated from adult fleas as follows. Approximately 100 mg of adult *C. felis* were crushed in a mortar & pestle using DNAzol™ reagent, available from Life Technologies, Rockville, Md., and genomic DNA was recovered according to manufacturer's instructions. Resultant DNA was resuspended in water.

A flea head and nerve cord RACE pool was constructed as follows. Approximately 140 female and 60 male adult *C. felis* heads and nerve cords were dissected from unfed fleas then ground to a homogenized powder by mortar and pestle in liquid nitrogen. Total RNA was isolated from the resulting homogenized powder using a modification of the acid-guanidinium-phenol-chloroform method described by Chomczynski et al., 1987, Anal. Biochem. 162, p. 156-159, which is incorporated herein by reference in its entirety. The modification of the method is that solution D described by Chomczynski et al. was changed to a solution of 4 M guanidine isothiocyanate, 25 mM Sodium Citrate pH 7.0, 1.5% Sarcosyl, 0.5 M 2-mercaptoethanol. Spectrophotometer and ethidium bromide stained denaturing gel analyses indicated that the yield of total RNA was approximately 27 μg. Approximately 6 μg of total RNA was used as template to construct a RACE pool using a Marathon cDNA Amplification Kit, available from Clontech Laboratories, Inc., Palo Alto, Calif., according to the manufacturer's instructions.

EXAMPLE 2

This example describes the cloning, sequencing and expression of flea octopamine receptor nucleic acid molecules.

Degenerate PCR primers designed using information from *Drosophila melanogaster* octopamine receptor OAMB were used to amplify an approximately 150 nucleotide product from genomic DNA of adult, unfed fleas prepared as described above. Forward primer 5' GTNGAYGTNT GGATGTGYAC 3', designated SEQ ID NO:14, was used in combination with reverse primer 5' TGGNGGRAAR CADATNAC 3', designated SEQ ID NO:15, in a PCR reaction using 50 ng of genomic DNA, 2.5 units (U) AmpliTaq polymerase, available from PE Biosystems, Foster City, Calif., 0.5 U Pfu polymerase, available from Stratagene, La Jolla, Calif., 0.2 mM dNTP's and 0.5 to 1.0 μM primers, in a total reaction volume of 50 μL. The following amplification conditions were used: (1) one cycle of 95° C. for 10 seconds, (2) five cycles of 94° C. for 10 seconds, 52° C. for 30 seconds, and 72° C. for 30 seconds, (3) thirty cycles of 94° C. for 10 seconds, 49° C. for 20 seconds, and 72° C. for 30 seconds. The resulting product, referred to as $nCfOCR_{111}$, was sequenced to reveal a 111 nucleotide product, having a coding strand designated SEQ ID NO:1 and a complementary strand designated SEQ ID NO:2.

First and second PCR reactions were performed on a flea cDNA library under the following reaction conditions: 2.5 U AmpliTaq polymerase per reaction, 0.2 mM dNTP's, and 0.5 to 1.0 μM primers, in a total reaction volume of 50 μL, were used under the following cycling conditions: (1) one cycle of 95° C. for one minute, (2) five cycles of 94° C. 10 seconds, 62° C. 30 seconds, and 72° C. for two minutes thirty seconds, (3) ten cycles of 94° C. for 10 sec, 59° C. for 30 seconds, and 72° C. for three minutes, (4) fifteen cycles of 94° C. for 10 sec, 56° C. for 30 seconds, and 72° C. for three minutes. In the first PCR reaction, a forward primer designed using the sequence information obtained from SEQ ID NO:1, having the sequence 5'ATGTGTGGAT GTGTACAGCT TC 3', designated SEQ ID NO:16 was used in combination with a primer designed to anneal to the 3' end of the vector region common to all cDNAs in the library, having the sequence 5'GTAATACGAC TCACTATAGG GC 3', designated SEQ ID NO:17. Three μL of a flea mixed instar cDNA library, prepared as described in U.S. Pat. No. 6,063,610 was used as template. Three μL of the resulting reaction product were used in a second PCR reaction using SEQ ID NO:17 as the reverse primer in combination with a forward primer designed using the sequence information obtained from SEQ ID NO:1, having the sequence 5' AAATCTGTGC GCAATATCCT TGG 3', designated SEQ ID NO:18. The resulting PCR product was excised from an agarose gel and T/A cloned using the TOPO T/A™ cloning kit, available from Invitrogen, Carlsbad, Calif. The purified product, denoted $nCfOCR_{2061}$, was sequenced and shown to contain 2061 base pairs, having a coding strand designated SEQ ID NO:3 and a complementary strand designated SEQ ID NO:5. Sequence analysis of SEQ ID NO:3 indicates that $nCfOCR_{2061}$ encodes a protein denoted $PCfOCR_{559}$, having a sequence represented by SEQ ID NO:4, assuming an open reading frame extending from nucleotide 3 through nucleotide 1679 of SEQ ID NO:3. Sequence analysis further demonstrated that SEQ ID NO:4 represents the C-terminus of a flea octopamine receptor.

A PCR reaction was performed to isolate the 5' portion of a flea octopamine receptor cDNA from the flea head and nerve cord RACE pool prepared as described in Example 1, as follows. Forward primer AP1, which corresponds to sequence within the adapter flanking the termini of all fragments in the flea head and nerve cord RACE pool, having nucleotide sequence 5' CCATCCTAAT ACGACTCACT ATAGGGC 3', designated SEQ ID NO:19, was used in combination with a reverse primer designed using the sequence information obtained from SEQ ID NO:1, having nucleotide sequence 5' GGAAGCAGAT CACAAAACTA AG 3', designated SEQ ID NO:20. The following PCR conditions were used: 2 U/50 µL reaction of AmpliTaq polymerase, 0.5 U Pfu polymerase, 0.2 mM dNTP's, 0.5 µM primers and 3 µL of a 1/250 dilution of the flea head & nerve cord RACE pool as the template, in a total reaction volume of 50 µL. Template DNA was added directly to the tubes in the PCR machine after the initial cycling temperature reached 72° C. The following amplification conditions were used (1) one cycle of 95° C. for 1 minute, (2) five cycles of 94° C. for 10 seconds, 58° C. for 30 seconds and 72° C. for 2 minutes, (3) thirty cycles of 94° C. for 10 seconds, 54° C. for 30 seconds, and 72° C. for 2 minutes and 30 seconds. The resulting PCR product was excised from an agarose gel and DNA purified using a QiaQuick™ Extraction Kit, available from Qiagen, Chatsworth, Calif. Two µL of this product was used as template for nested PCR with forward primer SEQ ID NO:19 and a reverse primer having nucleotide sequence 5' CCAAAGCCCG GCTATGAGTC CC 3', designated SEQ ID NO:21 using the reaction conditions set forth for the primary reaction. The following amplification conditions were used (1) one cycle of 95° C. for 1 minute, (2) five cycles of 94° C. for 10 seconds, 58° C. for 30 seconds and 72° C. for 1 minute, (3) thirty cycles of 94° C. for 10 seconds, 54° C. for 30 seconds, and 72° C. for 1 minute. The purified product, denoted nCfOCR$_{868}$, was sequenced and shown to contain 868 base pairs, having a coding strand designated SEQ ID NO:6 and a complementary strand designated SEQ ID NO:8. Sequence analysis of SEQ ID NO:6 indicates that nCfOCR$_{868}$ encodes a protein denoted PCfOCR$_{178}$, having a sequence represented by SEQ ID NO:7, assuming an open reading frame extending from nucleotide 333-866 of SEQ ID NO:6. Sequence analysis further demonstrated that SEQ ID NO:7 represents the N-terminus of a flea octopamine receptor.

Sequence information from SEQ ID NO:3 and SEQ ID NO:6 was used to design primers to amplify one contiguous piece of DNA encoding the entire open reading frame of the nucleic acid molecule encoding a flea octopamine receptor and a PCR reaction was conducted as follows. A forward primer having nucleotide sequence 5' AAGAATTCGA TAT-GAATGCC TCGGAGTACA TTAACACG 3', designated SEQ ID NO:22 and having an EcoRI site indicated in bold was used in conjunction with a reverse primer having nucleotide sequence, 5' TTCTCGAGCC TCTTGTGACA TCAT-TATCAC TATCTTG 3', designated SEQ ID NO:23 and having a XhoI site indicated in bold. The following reaction conditions were used: 2.5 U PfuTurbo™ polymerase per reaction and the manufacturers polymerase reaction buffer, available from Stratagene, 3 µL of a 1/50 dilution of flea head and nerve cord RACE pool as template, 0.2 mM dNTP, and 0.5 µM primers, in a total reaction volume of 50 µL. The following cycling conditions were used: (1) one cycle of 94° C. for 30 seconds, (2) five cycles of 94° C. for 10 seconds, 53° C. for 30 seconds, and 72° C. for 2 minutes, (3) thirty-six cycles of 94° C. for 10 seconds, 55° C. for 20 seconds, and 72° C. for 2 minutes and 30 seconds. The resulting approximately 2 Kb PCR product was excised from an agarose gel as described above and T/A cloned using a TOPO T/A cloning kit. The purified product was sequenced and shown to contain 2082 base pairs, having a coding strand designated SEQ ID NO:9 and a complementary strand designated SEQ ID NO:10.

A review of SEQ ID NOs. 3, 6, 9 and 10 revealed a sequence discrepancy in SEQ ID NOs. 9 and 10, possibly due to a PCR error, which resulted in an internal stop where a 'GGA' codon had been replaced with a 'TGA' codon. PCR mutagenesis was performed to correct the error in SEQ ID NO:9 by a standard method known as PCR overlap extension, as follows. A first PCR reaction was performed using a forward primer having the sequence 5' CAGAGCTATC AAC-CAAGGAT TCAGGACCAC AAAAGG 3', designated SEQ ID NO:24 and having a mutagenized region indicated in bold, was used in combination with a reverse primer corresponding to a region of vector sequence, having the sequence 5' CTTG-GTACCG AGCTCGGATC C 3', designated SEQ ID NO:25. A second PCR reaction was performed using a forward primer having the sequence 5'CCTTTTGTGG TCCT-GAATCC TTGGTTGATA GCTCTG 3', designated SEQ ID NO:26 and having a mutagenized region indicated in bold, in combination with a reverse primer corresponding to a region of vector sequence, having the sequence 5' AGATGCATGC TCGAGCGGCC G 3', designated SEQ ID NO:27. Each of these PCR reactions was performed using about 100 ng of a T/A clone containing SEQ ID NO:9 described above as template, 2.5 U PfuTurbo polymerase, 0.2 mM dNTP, and 0.5 µM primers, in a total reaction volume of 50 µL under the following cycling conditions: (1) one cycle of 95° C. for 30 seconds, (2) five cycles of 94° C. for 10 seconds, 56° C. for 30 seconds, 72° C. for 1 minute, (3) twenty-seven cycles of 94° C. for 10 seconds, 59° C. for 20 seconds, 72° C. for 2 minutes. These PCR reactions produced approximately 1300 base pair and 800 base pair products, respectively.

One µl of each of the 1300 base pair and 800 base pair PCR products described above were mixed and used as template in a final PCR reaction to regenerate a full length "repaired" version of SEQ ID NO:9, as follows. A forward primer with the sequence 5' ATGAATGCCT CGGAGTACAT TAACAC-GACA ACAATCAG 3', designated SEQ ID NO:28, was used in conjunction with a reverse primer having the sequence 5' TCATCTTGTG ACATCATTAT CACTATCTTG ACGAACG 3', designated SEQ ID NO:29, in a PCR reaction containing 2.5 U PfuTurbo polymerase, 0.2 mM dNTP, and 0.5 µM primers, in a total reaction volume of 50 µL, under the following cycling conditions: (1) one cycle of 95° C. for 30 seconds, (2) one cycle of 72° C. for 5 minutes, (3) five cycles of 94° C. for 10 seconds, 56° C. for 30 seconds, and 72° C. for 2 minutes, (4) twenty cycles of 94° C. for 10 seconds, 59° C. for 20 seconds, and 72° C. for 2 minutes and 30 seconds.

The resulting PCR product was excised from an agarose gel and run over a QiaQuick purification column, and found to contain an approximately 2100 base pair nucleic acid molecule. The resulting eluate was "polished" to facilitate T/A cloning of the fragment as follows: 43 µL of the total eluate of 50 µL was mixed with 5 µL of AmpliTaq™ PCR buffer, 0.1 µL of 25 mM dNTP mix, and 1 µL (5 U) of AmpliTaq polymerase and incubated at 72° C. for 8 minutes. Four µL of this reaction was used in a TOPO T/A cloning reaction performed as described above. The insert from a resulting T/A clone was sequenced which revealed that the error had been corrected.

The purified product, denoted nCfOCR$_{2136}$, was sequenced and shown to contain 2136 base pairs, having a coding strand designated SEQ ID NO:11 and a complementary strand designated SEQ ID NO:13. Sequence analysis of SEQ ID NO:11 indicates that nCfOCR$_{2136}$ encodes a protein denoted PCfOCR$_{712}$, having a sequence represented by SEQ ID NO:12, assuming a start codon spanning nucleotide 1 to nucleotide 3 and a final codon spanning nucleotide 2134 to nucleotide 2136 of SEQ ID NO:11.

Comparison of nucleic acid SEQ ID NO:11 with nucleic acid sequences reported in GenBank indicates that SEQ ID NO:11 shared the most similarity, i.e. about 49% with a *D. melanogaster* octopamine receptor nucleic acid molecule, OAMB (GenBank accession number AF065443). Comparison of amino acid sequence SEQ ID NO:12 with amino acid sequences reported in GenBank indicates that SEQ ID NO:12 showed the most similarity, i.e. about 55%, with the *Balanus amphitrite* G-protein coupled receptor (GenBank accession number Q93126).

EXAMPLE 3

This example describes the expression of a tagged flea octopamine receptor protein.

In order to clone the cDNA encoding SEQ ID NO:12 into the DES™ expression system, available from Invitrogen, with a C-terminal tag, the following PCR was performed. One µL of a T/A clone containing SEQ ID NO:11 was used as template in a PCR reaction containing 2.5 U PfuTurbo polymerase, 0.2 mM dNTP's, and 0.5 µM each of primer SEQ ID NO:22 and primer SEQ ID NO:23 described above under the following cycling conditions: (1) one cycle of 95° C. for 30 seconds, (2) five cycles of 94° C. for 10 seconds, 55° C. for 30 seconds, and 72° C. for 2 minutes, (3) twenty cycles of 94° C. for 10 seconds 59° C. for 20 seconds, and 72° C. for 2 minutes. The resultant nucleic acid molecule was excised from an agarose gel, prepared for cloning with a QiaQuick purification column, cut with enzymes EcoR1 and Xho1, re-purified over a QiaQuick column and ligated into a pAC-5.1/V5-His B expression vector, available from Invitrogen, that had also been cut with EcoR1 and Xho1. This vector encodes a protein with a His tag and a V5 tag at the carboxyl end. Ligation products were transformed into *E. coli* DH5α and transformant bacteria were screened for inserts by PCR and a clone containing an insert of the appropriate size was used to transfect *Drosophila* S-2 insect cells using the DES expression system, following manufacturer's protocols. This system utilizes co-transfection with a plasmid carrying the selectable marker blasticidin. CellFectin liposomal regent, available from Life Technologies, was used to deliver 5 µg of the above-mentioned plasmid DNA and 0.2 µg pCoBlast plasmid encoding the blasticidin resistance gene, available as part of the DES expression kit, into the cells. At two days post transfection, the cells were split approximately 1:2 and selection was performed for 5 days through the addition of 30 µg/mL blasticidin, available from Invitrogen, to the media. Following selection, expansion of the cells was performed without selection in shaker flasks. Cells were lysed in SDS-PAGE gel sample loading buffer and a Western blot was performed on cell lysates following separation by denaturing PAGE gel and blotting to a nitrocellulose membrane using techniques known to those skilled in the art. Anti-V5 antibody directed against a portion of the C-terminal fusion protein of the vector, available from Invitrogen, indicated expression of an approximately 90 kilodalton band, which corresponds to the approximate predicted size of a tagged flea octopamine receptor. A Western blot performed under the same conditions on cell lysates from untransfected cells did not contain a homologous 90 kilodalton band.

EXAMPLE 4

This example describes the preparation of tick genomic DNA and a tick head and nerve cord cDNA pool by Rapid Amplification of cDNA Ends (RACE pool).

Genomic DNA was isolated from adult ticks as follows. Four adult *Rhipicephalus sanguineus* were crushed in a mortar & pestle using DNAzol™ reagent, available from Life Technologies, Rockville, Md., and genomic DNA was recovered according to manufacturer's instructions. Resultant DNA was resuspended in 50 µL T. E. and had an estimated concentration of 50 ng/µL.

A tick cDNA RACE pool was constructed as follows. Approximately 10 unfed adult *Rhipicephalus sanguineus* were ground to a homogenized powder by mortar and pestle in liquid nitrogen. Total RNA was isolated from the resulting homogenized powder using a modification of the acid-guanidinium-phenol-chloroform method described by Chomczynski et al., 1987, Anal. Biochem. 162, p. 156-159, which is incorporated herein by reference in its entirety. The modification of the method is that solution D described by Chomczynski et al. was changed to a solution of 4 M guanidine isothiocyanate, 25 mM Sodium Citrate pH 7.0, 1.5% Sarcosyl, 0.5 M 2-mercaptoethanol. Spectrophotometer and ethidium bromide stained denaturing gel analyses indicated that the yield of total RNA was approximately 43 µg. Approximately 10 µg of total RNA was used as template to construct a RACE pool using a Marathon cDNA Amplification Kit, available from Clontech Laboratories, Inc., Palo Alto, Calif., according to the manufacturer's instructions.

EXAMPLE 5

This example describes the cloning and sequencing of tick octopamine receptor nucleic acid molecules.

PCR primers whose sequence was obtained from Van Poyer et al., Insect Biochemistry and Molecular Biology, 31 (2001) 333-338 were used to amplify an approximately 100 nucleotide product from genomic DNA of adult, unfed ticks prepared as described above. Forward primer 5' GCCAT-CATYG TGGGCRKSTT CATCKTBTGC TGG 3', designated SEQ ID NO:42, was used in combination with reverse primer 5' GATCATSGGR TTWAYGGCSG AGTTGCAGTA GCC 3', designated SEQ ID NO:43, in a PCR reaction using 2 uL of genomic DNA, 2.5 units (U) AmpliTaq polymerase, available from PE Biosystems, Foster City, Calif., 0.2 mM dNTP's and 1.0 µM primers, in a total reaction volume of 50 µL. The following amplification conditions were used: (1) one cycle of 95° C. for 1 minute, (2) five cycles of 94° C. for 10 seconds, 60° C. for 30 seconds, and 72° C. for 30 seconds, (3) ten cycles of 94° C. for 10 seconds, 57° C. for 30 seconds, and 72° C. for 30 seconds, (4) twenty-five cycles of 94° C. for 10 seconds, 54° C. for 30 seconds, and 72° C. for 45 seconds. The resulting product, referred to as nRsOCR$_{102}$, was excised from an agarose gel and T/A cloned using the Topo TA Cloning Kit™ from Invitrogen and sequenced to reveal a 102 nucleotide product, having a coding strand designated SEQ ID NO:30 and a complementary strand designated SEQ ID NO:32.

First and second PCR reactions were performed on the tick cDNA library prepared as described in Example 1 under the following reaction conditions: 2.5 U Advantage™ polymerase per reaction, available from Clonetech, Palo Alto, Calif., 0.2 mM dNTP's, and 0.5 µM primers, in a total reaction volume of 50 µL, were used under the following cycling conditions: (1) one cycle of 94° C. for 30 seconds, (2) five cycles of 94° C. for 5 seconds, 64° C. for 4 minutes, (3) five cycles of 94° C. for 5 seconds, 66° C. for 4 minutes, (4) five cycles of 94° C. for 5 seconds, 68° C. for 4 minutes, and (5) one cycle of 72° C. for three minutes. In the first PCR reaction, a forward primer having the sequence 5' GCTGGCT-GCC ATTCTTCACC GTG 3', designated SEQ ID NO:44 was used in combination with a primer corresponding to sequence within the adapter flanking the termini of all fragments in the cDNA RACE pool, having the sequence 5' CCATCCTAAT ACGACTCACT ATAGGGC 3', designated SEQ ID NO:45. Five μL of a 1/250 dilution of tick cDNA RACE pool was used as template. One μL of the resulting reaction product was used in a second PCR reaction using SEQ ID NO:45 as the reverse primer in combination with a forward primer having the sequence 5' GGTGCGTGCA TTCTGCGAGC ACTG 3', designated SEQ ID NO:46. The resulting PCR product was excised from an agarose gel and T/A cloned using the TOPO T/A™ cloning kit, available from Invitrogen, Carlsbad, Calif. The purified product, denoted nRsOCR$_{499}$, was sequenced and shown to contain 499 base pairs, having a coding strand designated SEQ ID NO:33 and a complementary strand designated SEQ ID NO:35. Sequence analysis of SEQ ID NO:33 indicates that nRsOCR$_{499}$ encodes a protein denoted PRsOCR$_{92}$, having a sequence represented by SEQ ID NO:34, assuming an open reading frame extending from nucleotide 3 through nucleotide 278 of SEQ ID NO:33. Sequence analysis further demonstrated that SEQ ID NO:34 represents the C-terminus of a tick octopamine receptor.

To isolate the 5' portion of a tick octopamine receptor, first and second PCR reactions were performed on the tick cDNA library prepared as described in Example 1 under the following reaction conditions: 2.5 U Advantage™ polymerase per reaction, 0.2 mM dNTP's, and 0.5 μM primers, in a total reaction volume of 50 μL, were used under the following cycling conditions: (1) one cycle of 95° C. for 1 minute, (2) five cycles of 94° C. for 10 seconds, 66° C. for 30 seconds, 72° C. for 1 minute, (3) thirty cycles of 94° C. for 10 seconds, 63° C. for 20 seconds, 72° C. for two minutes.

In the first PCR reaction, a forward primer SEQ ID NO:45 was used in combination with a reverse primer having nucleotide sequence 5' AGAAGACCGA GAACAGCAGG TTGG 3', designated SEQ ID NO:47. Three μL of a 1/250 dilution of tick cDNA RACE pool was used as template. One μL of the resulting reaction product was used as the template in a second PCR reaction using SEQ ID NO:45 as the reverse primer in combination with a forward primer having the sequence 5' TGGCACCAGG TGTGGCCGAA GAGCCACAC 3', designated SEQ ID NO:48. The resulting PCR product was excised from an agarose gel and T/A cloned using a TOPO T/A™ cloning kit. The purified product denoted nRsOCR$_{286}$, was sequenced and shown to contain 286 base pairs, having a coding strand designated SEQ ID NO:36 and a complementary strand designated SEQ ID NO:38. Sequence analysis of SEQ ID NO:36 indicates that nRsOCR$_{286}$ encodes a protein denoted PRsOCR$_{95}$, having a sequence represented by SEQ ID NO:37, assuming an open reading frame extending from nucleotide 1 through nucleotide 285 of SEQ ID NO:36.

Sequence analysis further demonstrated that SEQ ID NO:37 represents the N-terminus of a tick octopamine receptor.

Sequence information from SEQ ID NO:32 and SEQ ID NO:35 was used to design primers to amplify one contiguous piece of DNA encoding the entire open reading frame of the nucleic acid molecule encoding a tick octopamine receptor and a PCR reaction was conducted as follows. A forward primer having nucleotide sequence 5' ATGAACGAGA CGTGCCTGTC CCGC 3', designated SEQ ID NO:49 was used in conjunction with a reverse primer having nucleotide sequence, 5' CTAGGGCGAC GCGGCGTTGT CCGG 3', designated SEQ ID NO:50. The following reaction conditions were used: 2.5 U Advantage™ polymerase per reaction, five μL of a 1/250 dilution of tick cDNA RACE pool as template, 0.2 mM dNTP, and 0.5 μM primers, in a total reaction volume of 50 μL. The following cycling conditions were used: (1) one cycle of 94° C. for 5 minutes, (2) five cycles of 94° C. for 5 seconds, 72° C. for 2.5 minutes, (3) 5 cycles of 94° C. 5 seconds, 70° C. 2.5 minutes, (4) thirty-five cycles of 94° C. for 5 seconds, 68° C. for 2.5 minutes, and (5) one cycle of 72° C. for 7 minutes. The resulting approximately 1500 nucleotide PCR product was excised from an agarose gel, purified using a Qiaquick™ kit available from Qiagen, Chatsworth, Calif., and T/A cloned using a TOPO T/A cloning kit. The purified product, referred to as nRsOCR$_{1443}$ was sequenced and shown to contain 1443 base pairs, having a coding strand designated SEQ ID NO:39 and a complementary strand designated SEQ ID NO:41. Sequence analysis of SEQ ID NO:39 indicates that nRsOCR$_{1443}$ encodes a protein denoted PRsOCR$_{480}$, having a sequence represented by SEQ ID NO:40, assuming an open reading frame extending from nucleotide 1 through nucleotide 1440 of SEQ ID NO:39. Sequence analysis further demonstrated that SEQ ID NO:40 represents an open reading frame encoding a full-length tick octopamine receptor.

Comparison of nucleic acid SEQ ID NO:39 with nucleic acid sequences reported in GenBank indicates that SEQ ID NO:39 shared the most similarity, i.e. about 57% with a *Balanus amphitrite* gene for G protein-coupled receptor (GenBank accession number D78587). Comparison of amino acid sequence SEQ ID NO:40 with amino acid sequences reported in GenBank indicates that SEQ ID NO:40 showed the most similarity, i.e. about 52%, with an *Anopheles gambiae* str. PEST (genome seq conceptual translation) and a second highest similarity to a *Balanus amphitrite* G-protein coupled receptor (GenBank accession number BAA11424).

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated nucleic acid molecule selected from the group consisting of:
   (a) a nucleic acid molecule comprising a nucleic acid sequence that encodes a protein comprising SEQ ID NO:40; and
   (b) a nucleic acid molecule comprising a nucleic acid sequence fully complementary to the nucleic acid sequence of (a).

2. A recombinant molecule comprising a nucleic acid molecule as set forth in claim 1 operatively linked to a transcription control sequence.

3. A recombinant virus comprising a nucleic acid molecule as set forth in claim 1.

4. An isolated, recombinant cell comprising a nucleic acid molecule as set forth in claim 1.

5. The isolated nucleic acid molecule of claim 1, wherein said nucleic acid sequence is selected from the group consisting of SEQ ID NO:39 and SEQ ID NO:41.

6. An isolated nucleic acid molecule consisting of a nucleic acid sequence selected from the group consisting of:
   (a) a nucleic acid sequence that encodes a polypeptide consisting of SEQ ID NO: 34, SEQ ID NO:37 or SEQ ID NO:40; and
   (b) a nucleic acid sequence fully complementary to the nucleic acid sequence of (a).

7. The isolated nucleic acid molecule of claim 6, wherein said nucleic acid sequence is selected from the group consisting of SEQ ID NO: 33, SEQ ID NO: 35, SEQ ID NO: 36, SEQ ID NO: 38, SEQ ID NO: 39 and SEQ ID NO: 41.

* * * * *

SEQUENCE LISTING

```
<160> NUMBER OF SEQ ID NOS: 50

<210> SEQ ID NO 1
<211> LENGTH: 111
<212> TYPE: DNA
<213> ORGANISM: Ctenocephalides felis

<400> SEQUENCE: 1
gatatgtcgc tgtcaccagg ccagttgctt atccgagcat catgtctacg aaagggctaa      60
```

```
gggactcata gccgggcttt ggggttcttag ttttgtgatc tgcttcccac c          111
```

```
<210> SEQ ID NO 2
<211> LENGTH: 111
<212> TYPE: DNA
<213> ORGANISM: Ctenocephalides felis

<400> SEQUENCE: 2
ggtgggaagc agatcacaaa actaagaacc caaagcccgg ctatgagtcc cttagccctt   60
tcgtagacat gatgctcgga taagcaactg gcctggtgac agcgacatat c           111
```

```
<210> SEQ ID NO 3
<211> LENGTH: 2061
<212> TYPE: DNA
<213> ORGANISM: Ctenocephalides felis
<220> FEATURE:
<221> NAME/KEY: CDS
<222> LOCATION: (3)..(1679)
<220> FEATURE:
<221> NAME/KEY: misc_feature
<222> LOCATION: (192)..(192)
<223> OTHER INFORMATION: The "Xaa" at location 192 = Ala or Thr
<220> FEATURE:
<221> NAME/KEY: misc_feature
<222> LOCATION: (193)..(193)
<223> OTHER INFORMATION: The "Xaa" at location 193 = Asn or Tyr

<400> SEQUENCE: 3 at aga tat gtc gct gtc acc agg cca gtt gct tat ccg agc atc atg     47
   Arg Tyr Val Ala Val Thr Arg Pro Val Ala Tyr Pro Ser Ile Met
   1               5                   10                  15 tct acg aaa agg gct aag gga ctc ata gcc ggg ctt tgg gtt ctt agt    95
Ser Thr Lys Arg Ala Lys Gly Leu Ile Ala Gly Leu Trp Val Leu Ser
                20                  25                  30 ttt gtg ata tgc ttt cca cct tta gtc gga tgg aaa gat aaa aag gaa   143
Phe Val Ile Cys Phe Pro Pro Leu Val Gly Trp Lys Asp Lys Lys Glu
            35                  40                  45 tcc gag gat ctg ata gac ata tct tca tgt cct tgg acg tgc gag ttg   191
Ser Glu Asp Leu Ile Asp Ile Ser Ser Cys Pro Trp Thr Cys Glu Leu
        50                  55                  60 acg aac gat gca gga tat gtg gtg tat tct gct ctc gga tca ttc tac   239
Thr Asn Asp Ala Gly Tyr Val Val Tyr Ser Ala Leu Gly Ser Phe Tyr
    65                  70                  75 att cct atg ttt gtc atg tta ttt ttc tac tgg agg ata tat aga gca   287
Ile Pro Met Phe Val Met Leu Phe Phe Tyr Trp Arg Ile Tyr Arg Ala
80                  85                  90                  95 gct gtc agg aca acc aga gct atc aac caa gga ttc agg act aca aaa   335
Ala Val Arg Thr Thr Arg Ala Ile Asn Gln Gly Phe Arg Thr Thr Lys
                100                 105                 110 ggt tcg cgt ggt ata gga cga ttt gac gaa caa cgc cta act tta agg   383
Gly Ser Arg Gly Ile Gly Arg Phe Asp Glu Gln Arg Leu Thr Leu Arg
            115                 120                 125 att cat aga gga cgg ggt ggt tct gaa aat aga aga tgt cat cat cat   431
Ile His Arg Gly Arg Gly Gly Ser Glu Asn Arg Arg Cys His His His
        130                 135                 140 tct tcc att aaa agt aat gct tca ggg aga atg tct aca tct aca tct   479
Ser Ser Ile Lys Ser Asn Ala Ser Gly Arg Met Ser Thr Ser Thr Ser
    145                 150                 155 atg agg aat tgt tct cct caa cat agt tca cca cgt agt gca agt acc   527
Met Arg Asn Cys Ser Pro Gln His Ser Ser Pro Arg Ser Ala Ser Thr
160                 165                 170                 175 agc tta gga agt act cac gaa tca cct gaa aaa tca tct ata tca agg   575
Ser Leu Gly Ser Thr His Glu Ser Pro Glu Lys Ser Ser Ile Ser Arg
                180                 185                 190
```

-continued

| | | |
|---|---|---|
| rcc wac acc tgg gtt ttg cat cat gcg acc aat aat tcc aat tca gga<br>Xaa Xaa Thr Trp Val Leu His His Ala Thr Asn Asn Ser Asn Ser Gly<br>                195                        200                    205 | 623 |
| gct tgt aac caa gtc gtc att gcc aat aat aca agt caa agt gca cca<br>Ala Cys Asn Gln Val Val Ile Ala Asn Asn Thr Ser Gln Ser Ala Pro<br>        210                       215                      220 | 671 |
| aac aat aat cag tta aat agt acc cag cct gar gtc act gtg aca aaa<br>Asn Asn Asn Gln Leu Asn Ser Thr Gln Pro Glu Val Thr Val Thr Lys<br>            225                       230                    235 | 719 |
| agt agt cga aga tct tcg aaa tca tat aag agc ttt aaa aag gaa aga<br>Ser Ser Arg Arg Ser Ser Lys Ser Tyr Lys Ser Phe Lys Lys Glu Arg<br>240                      245                       250                   255 | 767 |
| gtt caa att tcg gtg cag tat cca agt gca gaa aga ctt gat gaa ttg<br>Val Gln Ile Ser Val Gln Tyr Pro Ser Ala Glu Arg Leu Asp Glu Leu<br>                          260                       265                    270 | 815 |
| gaa ggt gaa tta gaa ggt gat gct aca aac aac atg tac acc gtc cac<br>Glu Gly Glu Leu Glu Gly Asp Ala Thr Asn Asn Met Tyr Thr Val His<br>               275                       280                    285 | 863 |
| tac tct gtg tcc aat ggt aac agc ttg tca aat cat tcg ttg atg cca<br>Tyr Ser Val Ser Asn Gly Asn Ser Leu Ser Asn His Ser Leu Met Pro<br>          290                       295                      300 | 911 |
| gag cag caa ata gtc gat tct tcg agc caa caa cag acc att aga gca<br>Glu Gln Gln Ile Val Asp Ser Ser Ser Gln Gln Gln Thr Ile Arg Ala<br>305                      310                       315 | 959 |
| aca aca aca att aac ggt gat cag caa tta aat tcg ggt tcc atc tat<br>Thr Thr Thr Ile Asn Gly Asp Gln Gln Leu Asn Ser Gly Ser Ile Tyr<br>320                      325                       330                 335 | 1007 |
| cgg cca cag gat aat cat cat ctc cga gtt acg tcg caa aga ttg gca<br>Arg Pro Gln Asp Asn His His Leu Arg Val Thr Ser Gln Arg Leu Ala<br>                        340                       345                    350 | 1055 |
| ccg tcg cct aca ctg tcg aag gga atg cat agg cga tcc agc agc tgc<br>Pro Ser Pro Thr Leu Ser Lys Gly Met His Arg Arg Ser Ser Ser Cys<br>                 355                       360                    365 | 1103 |
| gat agt aga gat ttg gct ggg ttt caa tta tgc gaa agt tca agt cca<br>Asp Ser Arg Asp Leu Ala Gly Phe Gln Leu Cys Glu Ser Ser Ser Pro<br>                        370                       375                    380 | 1151 |
| agt cca aca aga agg ata atg tct gga agt ctt tat cgt gat gat agc<br>Ser Pro Thr Arg Arg Ile Met Ser Gly Ser Leu Tyr Arg Asp Asp Ser<br>385                      390                       395 | 1199 |
| gag tta ggt tcg act tcc aaa ctg cag cag caa aat aga aaa atg ggc<br>Glu Leu Gly Ser Thr Ser Lys Leu Gln Gln Gln Asn Arg Lys Met Gly<br>400                      405                       410                   415 | 1247 |
| aaa cgt aat ata aaa gct cag gtg aaa cgg ttt cga atg gag acg aaa<br>Lys Arg Asn Ile Lys Ala Gln Val Lys Arg Phe Arg Met Glu Thr Lys<br>                    420                       425                    430 | 1295 |
| gct gcc aaa aca ctt gca ata att gtc ggt ggt ttt att gta tgc tgg<br>Ala Ala Lys Thr Leu Ala Ile Ile Val Gly Gly Phe Ile Val Cys Trp<br>                 435                       440                    445 | 1343 |
| ttt ccc ttt ttc aca atg tac gta ata aga gca ttt tgt cca gac tgc<br>Phe Pro Phe Phe Thr Met Tyr Val Ile Arg Ala Phe Cys Pro Asp Cys<br>                 450                       455                    460 | 1391 |
| att cat cct gtt ctc ttc tcg gtt cta ttc tgg ctc ggc tac tgc aat<br>Ile His Pro Val Leu Phe Ser Val Leu Phe Trp Leu Gly Tyr Cys Asn<br>465                      470                       475 | 1439 |
| tct gcc atc aat ccg ctg att tat gca ctt ttt agc aaa gat ttc aga<br>Ser Ala Ile Asn Pro Leu Ile Tyr Ala Leu Phe Ser Lys Asp Phe Arg<br>480                      485                       490                   495 | 1487 |
| tac gcc ttc aag cgc atc att tgc aga tac tgc ttt tgt tgc ggt aat<br>Tyr Ala Phe Lys Arg Ile Ile Cys Arg Tyr Cys Phe Cys Cys Gly Asn<br>                 500                       505                    510 | 1535 |

-continued

```
cgt acc gag gcc cag cac agc ggt gga gct ggt ggt tct aga aga ggg    1583
Arg Thr Glu Ala Gln His Ser Gly Gly Ala Gly Gly Ser Arg Arg Gly
        515                 520                 525 tcc gat gga tct caa atg aaa act aat ttt agg ttt aat acc agt ttt    1631
Ser Asp Gly Ser Gln Met Lys Thr Asn Phe Arg Phe Asn Thr Ser Phe
    530                 535                 540 aat acc aaa aac tgc gtt cgt caa gat agt gat aat gat gtc aca aga    1679
Asn Thr Lys Asn Cys Val Arg Gln Asp Ser Asp Asn Asp Val Thr Arg
545                 550                 555 tgacccgcag ctaatgtggg attgcagagt cgagtttgaa aaaagtctag tctcaaaatc    1739
tgtgcaatct tgtgaattaa aaggagtgaa taaagacaat cgtagagtgc cgtaaaaata    1799
ttttcatata atgaaaataa atcgtgaata tatcaaaaat aaattgtata agattgcatg    1859
taaatttaca gaaaattctt ccaaagtttt atcaatgttg gattatataa aatatgtcat    1919
gtaagtttta ttgagcaagc atttcaattt attgcctaaa tacaagtttt gttttcaata    1979
taaaatataa aatataaaaa ctgatgtaaa tagatgaaaa aataaattgt tatatttgaa    2039
taactaaaaa aaaaaaaaaa aa                                            2061
```

<210> SEQ ID NO 4
<211> LENGTH: 559
<212> TYPE: PRT
<213> ORGANISM: Ctenocephalides felis
<220> FEATURE:
<221> NAME/KEY: misc_feature
<222> LOCATION: (192)..(192)
<223> OTHER INFORMATION: The 'Xaa' at location 192 stands for Ala, or
      Thr.
<220> FEATURE:
<221> NAME/KEY: misc_feature
<222> LOCATION: (193)..(193)
<223> OTHER INFORMATION: The 'Xaa' at location 193 stands for Asn, or
      Tyr.

<400> SEQUENCE: 4

```
Arg Tyr Val Ala Val Thr Arg Pro Val Ala Tyr Pro Ser Ile Met Ser
1               5                   10                  15

Thr Lys Arg Ala Lys Gly Leu Ile Ala Gly Leu Trp Val Leu Ser Phe
            20                  25                  30

Val Ile Cys Phe Pro Pro Leu Val Gly Trp Lys Asp Lys Lys Glu Ser
        35                  40                  45

Glu Asp Leu Ile Asp Ile Ser Ser Cys Pro Trp Thr Cys Glu Leu Thr
    50                  55                  60

Asn Asp Ala Gly Tyr Val Val Tyr Ser Ala Leu Gly Ser Phe Tyr Ile
65                  70                  75                  80

Pro Met Phe Val Met Leu Phe Phe Tyr Trp Arg Ile Tyr Arg Ala Ala
                85                  90                  95

Val Arg Thr Thr Arg Ala Ile Asn Gln Gly Phe Arg Thr Thr Lys Gly
            100                 105                 110

Ser Arg Gly Ile Gly Arg Phe Asp Glu Gln Arg Leu Thr Leu Arg Ile
        115                 120                 125

His Arg Gly Arg Gly Gly Ser Glu Asn Arg Arg Cys His His Ser
    130                 135                 140

Ser Ile Lys Ser Asn Ala Ser Gly Arg Met Ser Thr Ser Thr Ser Met
145                 150                 155                 160

Arg Asn Cys Ser Pro Gln His Ser Ser Pro Arg Ser Ala Ser Thr Ser
                165                 170                 175

Leu Gly Ser Thr His Glu Ser Pro Glu Lys Ser Ser Ile Ser Arg Xaa
            180                 185                 190
```

```
Xaa Thr Trp Val Leu His His Ala Thr Asn Asn Ser Asn Ser Gly Ala
    195                 200                 205

Cys Asn Gln Val Val Ile Ala Asn Asn Thr Ser Gln Ser Ala Pro Asn
210                 215                 220

Asn Asn Gln Leu Asn Ser Thr Gln Pro Glu Val Thr Val Thr Lys Ser
225                 230                 235                 240

Ser Arg Arg Ser Ser Lys Ser Tyr Lys Ser Phe Lys Lys Glu Arg Val
            245                 250                 255

Gln Ile Ser Val Gln Tyr Pro Ser Ala Glu Arg Leu Asp Glu Leu Glu
            260                 265                 270

Gly Glu Leu Glu Gly Asp Ala Thr Asn Asn Met Tyr Thr Val His Tyr
        275                 280                 285

Ser Val Ser Asn Gly Asn Ser Leu Ser Asn His Ser Leu Met Pro Glu
    290                 295                 300

Gln Gln Ile Val Asp Ser Ser Gln Gln Thr Ile Arg Ala Thr
305                 310                 315                 320

Thr Thr Ile Asn Gly Asp Gln Gln Leu Asn Ser Gly Ser Ile Tyr Arg
                325                 330                 335

Pro Gln Asp Asn His His Leu Arg Val Thr Ser Gln Arg Leu Ala Pro
                340                 345                 350

Ser Pro Thr Leu Ser Lys Gly Met His Arg Arg Ser Ser Ser Cys Asp
            355                 360                 365

Ser Arg Asp Leu Ala Gly Phe Gln Leu Cys Glu Ser Ser Ser Pro Ser
    370                 375                 380

Pro Thr Arg Arg Ile Met Ser Gly Ser Leu Tyr Arg Asp Asp Ser Glu
385                 390                 395                 400

Leu Gly Ser Thr Ser Lys Leu Gln Gln Asn Arg Lys Met Gly Lys
            405                 410                 415

Arg Asn Ile Lys Ala Gln Val Lys Arg Phe Arg Met Glu Thr Lys Ala
                420                 425                 430

Ala Lys Thr Leu Ala Ile Ile Val Gly Gly Phe Ile Val Cys Trp Phe
            435                 440                 445

Pro Phe Phe Thr Met Tyr Val Ile Arg Ala Phe Cys Pro Asp Cys Ile
        450                 455                 460

His Pro Val Leu Phe Ser Val Leu Phe Trp Leu Gly Tyr Cys Asn Ser
465                 470                 475                 480

Ala Ile Asn Pro Leu Ile Tyr Ala Leu Phe Ser Lys Asp Phe Arg Tyr
                485                 490                 495

Ala Phe Lys Arg Ile Ile Cys Arg Tyr Cys Phe Cys Cys Gly Asn Arg
            500                 505                 510

Thr Glu Ala Gln His Ser Gly Gly Ala Gly Gly Ser Arg Arg Gly Ser
        515                 520                 525

Asp Gly Ser Gln Met Lys Thr Asn Phe Arg Phe Asn Thr Ser Phe Asn
    530                 535                 540

Thr Lys Asn Cys Val Arg Gln Asp Ser Asp Asn Asp Val Thr Arg
545                 550                 555

<210> SEQ ID NO 5
<211> LENGTH: 2061
<212> TYPE: DNA
<213> ORGANISM: Ctenocephalides felis

<400> SEQUENCE: 5 ttttttttt  ttttttagt  tattcaaata  taacaattta  ttttttcatc  tatttacatc     60
```

```
agttttttata ttttatattt tatattgaaa acaaaacttg tatttaggca ataaattgaa        120
atgcttgctc aataaaactt acatgacata ttttatataa tccaacattg ataaaacttt        180
ggaagaattt tctgtaaatt tacatgcaat cttatacaat ttattttga tatattcacg        240 atttattttc attatatgaa aatattttta cggcactcta cgattgtctt tattcactcc        300
ttttaattca caagattgca cagattttga gactagactt ttttcaaact cgactctgca        360
atcccacatt agctgcgggt catcttgtga catcattatc actatcttga cgaacgcagt        420
ttttggtatt aaaactggta ttaaacctaa aattagtttt catttgagat ccatcggacc        480
ctcttctaga accaccagct ccaccgctgt gctgggcctc ggtacgatta ccgcaacaaa        540
agcagtatct gcaaatgatg cgcttgaagg cgtatctgaa atctttgcta aaaagtgcat        600
aaatcagcgg attgatggca gaattgcagt agccgagcca aatagaacc gagaagagaa         660 caggatgaat gcagtctgga caaaatgctc ttattacgta cattgtgaaa aagggaaacc        720
agcatacaat aaaaccaccg acaattattg caagtgtttt ggcagctttc gtctccattc        780
gaaaccgttt cacctgagct tttatattac gtttgcccat ttttctattt tgctgctgca        840
gtttggaagt cgaacctaac tcgctatcat cacgataaag acttccagac attatccttc        900
ttgttggact tggacttgaa ctttcgcata attgaaaccc agccaaatct ctactatcgc        960
agctgctgga tcgcctatgc attcccttcg acagtgtagg cgacggtgcc aatctttgcg       1020
acgtaactcg gagatgatga ttatcctgtg gccgatagat ggaacccgaa tttaattgct       1080
gatcaccgtt aattgttgtt gttgctctaa tggtctgttg ttggctcgaa gaatcgacta       1140
tttgctgctc tggcatcaac gaatgatttg acaagctgtt accattggac acagagtagt       1200
ggacggtgta catgttgttt gtagcatcac cttctaattc accttccaat tcatcaagtc       1260
tttctgcact tggatactgc accgaaattt gaactctttc cttttttaaag ctcttatatg       1320 atttcgaaga tcttcgacta cttttttgtca cagtgacytc aggctgggta ctatttaact       1380
gattattgtt tggtgcactt tgacttgtat tattggcaat gacgacttgg ttacaagctc       1440
ctgaattgga attattggtc gcatgatgca aaacccaggt gtwggycctt gatatagatg       1500 attttttcagg tgattcgtga gtacttccta agctggtact tgcactacgt ggtgaactat       1560
gttgaggaga acaattcctc atagatgtag atgtagacat tctccctgaa gcattacttt       1620
taatggaaga atgatgatga catcttctat tttcagaacc accccgtcct ctatgaatcc       1680
ttaaagttag gcgttgttcg tcaaatcgtc ctataccacg cgaaccttt gtagtcctga        1740 atccttggtt gatagctctg gttgtcctga cagctgctct atatatcctc cagtagaaaa       1800
atccttggtt gatagctctg gttgtcctga cagctgctct atatatcctc cagtagaaaa       1800
ataacatgac aaacatagga atgtagaatg atccgagagc agaatacacc acatatcctg       1860
catcgttcgt caactcgcac gtccaaggac atgaagatat gtctatcaga tcctcggatt       1920
cctttttatc tttccatccg actaaaggtg gaaagcatat cacaaaacta agaacccaaa       1980
gcccggctat gagtccctta gccctttcg tagacatgat gctcggataa gcaactggcc       2040
tggtgacagc gacatatcta t                                                 2061
```

<210> SEQ ID NO 6
<211> LENGTH: 868
<212> TYPE: DNA
<213> ORGANISM: Ctenocephalides felis
<220> FEATURE:
<221> NAME/KEY: CDS
<222> LOCATION: (333)..(866)

<400> SEQUENCE: 6

```
catcctaata cgactcacta tagggctcga gcggccgccc gggcaggtct agaattcagc         60
```

```
ggccgctgaa ttctaggtga tattgtatgt tcatgttagt gtgctcaacc tatacaaata      120
atgtggattt taaactcaa gaacaagtaa aaccaaaact aagtgttaaa tatattaaag       180
tatacaaaat attatacaag atatgcctaa caaatatatt aaaggaaagt atactaaaaa      240
tgctttaaat ataaatcagt tccctcctcg attttggctt gatgtcgcat taataaaaat      300
tatgtctata aattaaagaa aaagttctaa tt atg aat gcc tcg gag tac att       353
                                    Met Asn Ala Ser Glu Tyr Ile
                                     1               5
```

| | | | | | | | | | | | | | | | | |
|---|---|---|---|---|---|---|---|---|---|---|---|---|---|---|---|---|
| aac | acg | aca | aca | atc | agg | cta | agt | tat | ggg | act | tcc | tta | tct | ggg | gca | 401 |
| Asn | Thr | Thr | Thr | Ile | Arg | Leu | Ser | Tyr | Gly | Thr | Ser | Leu | Ser | Gly | Ala | |
| | | 10 | | | | 15 | | | | 20 | | | | | | |

```
acc att acc aca gga cac gga aat tct aca acg ttg tac aac cat gat       449
Thr Ile Thr Thr Gly His Gly Asn Ser Thr Thr Leu Tyr Asn His Asp
    25              30                  35 ggg act gaa tgt cct caa att gaa aat gtg gat tgg ctg agt cct tct       497
Gly Thr Glu Cys Pro Gln Ile Glu Asn Val Asp Trp Leu Ser Pro Ser
40              45                  50                  55 tcc ttg gca agt ctc acg gtt ttg ctg acc att gat ttg ctg gtg atc       545
Ser Leu Ala Ser Leu Thr Val Leu Leu Thr Ile Asp Leu Leu Val Ile
            60                  65                  70 ctg gga aat tgt ctg gtg ata gca gcc gtg ttc tgc tcc agc aaa ctg       593
Leu Gly Asn Cys Leu Val Ile Ala Ala Val Phe Cys Ser Ser Lys Leu
        75                  80                  85 cgc agt gtg acc aac ttg ttc ata gtg tca ctt gcc gtc gcc gat ttg       641
Arg Ser Val Thr Asn Leu Phe Ile Val Ser Leu Ala Val Ala Asp Leu
    90                  95                  100 atg gtc ggc atc gcg gtt ttg cct ttt agc gca act tgg gaa gtc ttc       689
Met Val Gly Ile Ala Val Leu Pro Phe Ser Ala Thr Trp Glu Val Phe
105                 110                 115 aag gtt tgg ata ttc gga agc agc tgg tgc aga gcc tgg tta gcc ctg       737
Lys Val Trp Ile Phe Gly Ser Ser Trp Cys Arg Ala Trp Leu Ala Leu
120                 125                 130                 135 gac gtg tgg atg tgc aca gct tcg ata tta aat ctg tgc gca ata tcc       785
Asp Val Trp Met Cys Thr Ala Ser Ile Leu Asn Leu Cys Ala Ile Ser
                140                 145                 150 ttg gat aga tat gtc gct gtc acc agg cca gtt gct tat ccg agc atc       833
Leu Asp Arg Tyr Val Ala Val Thr Arg Pro Val Ala Tyr Pro Ser Ile
            155                 160                 165 atg tct acg aaa ggg gct aag gga ttc ata gcc gg                         868
Met Ser Thr Lys Gly Ala Lys Gly Phe Ile Ala
            170                 175

<210> SEQ ID NO 7
<211> LENGTH: 178
<212> TYPE: PRT
<213> ORGANISM: Ctenocephalides felis

<400> SEQUENCE: 7

Met Asn Ala Ser Glu Tyr Ile Asn Thr Thr Thr Ile Arg Leu Ser Tyr
1               5                   10                  15

Gly Thr Ser Leu Ser Gly Ala Thr Ile Thr Thr Gly His Gly Asn Ser
            20                  25                  30

Thr Thr Leu Tyr Asn His Asp Gly Thr Glu Cys Pro Gln Ile Glu Asn
        35                  40                  45

Val Asp Trp Leu Ser Pro Ser Ser Leu Ala Ser Leu Thr Val Leu Leu
    50                  55                  60

Thr Ile Asp Leu Leu Val Ile Leu Gly Asn Cys Leu Val Ile Ala Ala
65                  70                  75                  80
```

```
Val Phe Cys Ser Ser Lys Leu Arg Ser Val Thr Asn Leu Phe Ile Val
                 85                  90                  95

Ser Leu Ala Val Ala Asp Leu Met Val Gly Ile Ala Val Leu Pro Phe
            100                 105                 110

Ser Ala Thr Trp Glu Val Phe Lys Val Trp Ile Phe Gly Ser Ser Trp
        115                 120                 125

Cys Arg Ala Trp Leu Ala Leu Asp Val Trp Met Cys Thr Ala Ser Ile
    130                 135                 140

Leu Asn Leu Cys Ala Ile Ser Leu Asp Arg Tyr Val Ala Val Thr Arg
145             150                 155                 160

Pro Val Ala Tyr Pro Ser Ile Met Ser Thr Lys Gly Ala Lys Gly Phe
                165                 170                 175

Ile Ala

<210> SEQ ID NO 8
<211> LENGTH: 868
<212> TYPE: DNA
<213> ORGANISM: Ctenocephalides felis

<400> SEQUENCE: 8
ccggctatga atcccttagc ccctttcgta gacatgatgc tcggataagc aactggcctg      60
gtgacagcga catatctatc caaggatatt gcgcacagat taatatcga agctgtgcac     120 atccacacgt ccagggctaa ccaggctctg caccagctgc ttccgaatat ccaaaccttg     180
aagacttccc aagttgcgct aaaaggcaaa accgcgatgc cgaccatcaa atcggcgact     240
gcaagtgaca ctatgaacaa gttggtcaca ctgcgcagtt tgctggagca gaacacggct     300
gctatcacca gacaatttcc caggatcacc agcaaatcaa tggtcagcaa accgtgaga     360 cttgccaagg aagaaggact cagccaatcc acattttcaa tttgaggaca ttcagtccca     420
tcatggttgt acaacgttgt agaatttccg tgtcctgtgg taatggttgc cccagataag     480
gaagtcccat aacttagcct gattgttgtc gtgttaatgt actccgaggc attcataatt     540 agaactttt ctttaattta tagacataat ttttattaat gcgacatcaa gccaaaatcg     600
aggagggaac tgatttatat ttaaagcatt tttagtatac tttcctttaa tatatttgtt     660
aggcatatct tgtataatat tttgtatact ttaatatatt taacacttag ttttggtttt     720
acttgttctt gagttataaa atccacatta tttgtatagg ttgagcacac taacatgaac     780
atacaatatc acctagaatt cagcggccgc tgaattctag acctgcccgg cggccgctc     840 gagccctata gtgagtcgta ttaggatg                                        868

<210> SEQ ID NO 9
<211> LENGTH: 2082
<212> TYPE: DNA
<213> ORGANISM: Ctenocephalides felis

<400> SEQUENCE: 9
acaacaatca ggctaagtta tgggacttcc ttatctgggg caaccattac cacaggacag      60
ggaaattcga caactttgta caaccatgat gggactgaat gtcctcaaat tgaaaatgtc     120
gactggctga gtccttcttc cttagcaagt ctcacggttt tgctgaccat cgatttgctg     180
gtgatcctgg gaaattgtct ggtgatagca gccgtgttct gctccagcaa actgcgcagt     240
gtgaccaact tgttcatagt gtcacttgca gtcgccgatt tgatggtcgg catcgcggtt     300 ttgccttta gcgcaacttg ggaagtcttc aaggtttgga tattcggaag cagctggtgc     360
cgagcctggt tagccctgga cgtgtggatg tgcacagctt cgatattaaa tctgtgcgca     420
```

-continued

| | |
|---|---|
| atatccttgg atagatatgt cgctgtcacc aggccagttg cttatccgag catcatgtct | 480 |
| acgaaaaggg ctaagggact catagccggg ctttggggttc ttagttttgt gatatgtttt | 540 |
| ccacctttag tcggatggaa ggataaaaag gaatccgagg atctgataga catatcttca | 600 |
| tgtccgtgga cgtgcgagtt gacgaatgat gcaggatatg tggtgtattc tgctctagga | 660 |
| tcattctaca ttcctatgtt tgtcatgtta ttttctact ggaggatata tagagcagct | 720 |
| gtcaggacaa ccagagctat caaccaatga ttcaggacca caaaaggttc gcgtggtata | 780 |
| ggacgatttg acgaacaacg cctaaccttta aggattcata gaggacgggg tggttctgaa | 840 |
| aatagaagat gtcatcatca ttcttccatt aaaagcaatg cttcagggag aatgtctaca | 900 |
| tctacttcta tgaggaattg ttctccacaa catagttcac cacgtagtgc aagtaccagc | 960 |
| ttaggaagta ctcacgaatc acctgaaaaa tcatctatat caaggaccaa cacctgggtt | 1020 |
| ttgcatcatg cgaccaataa ttccaattct ggagcttgta accaagtagt tatcgccaat | 1080 |
| aatacaagtc aaagtgcacc aaacaatcag ttaaatagta gtgcccagcc tgaagtcact | 1140 |
| gtaacaaaaa gtagtcgaag atcttcgaaa tcatataaga gctttaagaa ggaaagagtt | 1200 |
| caaatttcgg tgcagtatcc aagtgcagaa agacttgatg aattggaagg tgaattagaa | 1260 |
| ggtgatgcta caaacaacat gtacaccgtc cactactctg tgtccaatgg taacagcttg | 1320 |
| tcaaatcatt cgttgatgcc agagcagcaa atagtcgatt cttcgagcca caacagacc | 1380 |
| attaagcaac aacaacaatt aacggtgaat cagcaattaa attcgggttc catctatcgg | 1440 |
| ccacaggata tcatcatct ccagttacg tcgcaaagat tggcaccgtc gcctacactg | 1500 |
| tcgaagggaa tgcataggcg atccagcagc tgcgatagta gagatttggc tgggtttcaa | 1560 |
| ttatgcgaaa gttcaagtcc aagtccaaca agaaggataa tgtctggaag tctttatcgt | 1620 |
| gatgatagcg agttaggttc gacttccaaa ctgcagcagc aaaatagaaa aatgggcaaa | 1680 |
| cgtaatataa aagctcaggt gaaacggttt cgaatggaga cgaaagctgc caaaacactt | 1740 |
| gcaataattg tcggtggttt tattgtatgc tggtttccct ttttcacaat gtacgtaata | 1800 |
| agagcatttt gtccgactg cattcatcct gttctcttct cggttctatt ctggctcggc | 1860 |
| tactgcaatt ctgccatcaa tccgctgatt tatgcacttt ttagcaaaga ttttagatac | 1920 |
| gccttcaagc gcatcatttg cagatactgc ttttgttgcg gtaatcgtac cgaggcccag | 1980 |
| cacagcggtg gagctggtgg ttctagaaga gggtccgatg gatctcaaat gaaaactaat | 2040 |
| tttaggttta ataccagttt taataccaaa aactgcgttc gt | 2082 |

<210> SEQ ID NO 10
<211> LENGTH: 2082
<212> TYPE: DNA
<213> ORGANISM: Ctenocephalides felis

<400> SEQUENCE: 10

| | |
|---|---|
| acgaacgcag tttttggtat taaaactggt attaaaccta aaattagttt tcatttgaga | 60 |
| tccatcggac cctcttctag aaccaccagc tccaccgctg tgctgggcct cggtacgatt | 120 |
| accgcaacaa aagcagtatc tgcaaatgat gcgcttgaag gcgtatctaa aatctttgct | 180 |
| aaaaagtgca taaatcagcg gattgatggc agaattgcag tagccgagcc agaatagaac | 240 |
| cgagaagaga acaggatgaa tgcagtctgg acaaaatgct cttattacgt acattgtgaa | 300 |
| aaagggaaac cagcatacaa taaaaccacc gacaattatt gcaagtgttt tggcagcttt | 360 |
| cgtctccatt cgaaaccgtt tcacctgagc ttttatatta cgtttgccca ttttttctatt | 420 |
| ttgctgctgc agtttggaag tcgaacctaa ctcgctatca tcacgataaa gacttccaga | 480 |

-continued

| | |
|---|---|
| cattatcctt cttgttggac ttggacttga actttcgcat aattgaaacc cagccaaatc | 540 |
| tctactatcg cagctgctgg atcgccatgc cattcccttc gacagtgtag gcgacggtgc | 600 |
| caatctttgc gacgtaactc ggagatgatg attatcctgt ggccgataga tggaacccga | 660 |
| atttaattgc tgattcaccg ttaattgttg ttgttgctta atggtctgtt gttggctcga | 720 |
| agaatcgact atttgctgct ctggcatcaa cgaatgattt gacaagctgt taccattgga | 780 |
| cacagagtag tggacggtgt acatgttgtt tgtagcatca ccttctaatt cacctttccaa | 840 |
| ttcatcaagt ctttctgcac ttggatactg caccgaaatt tgaactcttt ccttcttaaa | 900 |
| gctcttatat gatttcgaag atcttcgact acttttttgtt acagtgactt caggctgggc | 960 |
| actactattt aactgattgt ttggtgcact ttgacttgta ttattggcga taactacttg | 1020 |
| gttacaagct ccagaattgg aattattggt cgcatgatgc aaaacccagg tgttggtcct | 1080 |
| tgatatagat gattttttcag gtgattcgtg agtacttcct aagctggtac ttgcactacg | 1140 |
| tggtgaacta tgttgtggag aacaattcct catagaagta gatgtagaca ttctcccctga | 1200 |
| agcattgctt ttaatggaag aatgatgatg acatcttcta ttttcagaac caccccgtcc | 1260 |
| tctatgaatc cttaaagtta ggcgttgttc gtcaaatcgt cctataccac gcgaaccttt | 1320 |
| tgtggtcctg aatcattggt tgatagctct ggttgtcctg acagctgctc tatatatcct | 1380 |
| ccagtagaaa aataacatga caaacatagg aatgtagaat gatcctagag cagaatacac | 1440 |
| cacatatcct gcatcattcg tcaactcgca cgtccacgga catgaagata tgtctatcag | 1500 |
| atcctcggat tccttttttat ccttccatcc gactaaaggt ggaaaacata tcacaaaact | 1560 |
| aagaacccaa agcccggcta tgagtcccctt agccctttttc gtagacatga tgctcggata | 1620 |
| agcaactggc ctggtgacag cgacatatct atccaaggat attgcgcaca gatttaatat | 1680 |
| cgaagctgtg cacatccaca cgtccagggc taaccaggct cggcaccagc tgcttccgaa | 1740 |
| tatccaaacc ttgaagactt cccaagttgc gctaaaaggc aaaaccgcga tgccgaccat | 1800 |
| caaatcggcg actgcaagtg acactatgaa caagttggtc acactgcgca gtttgctgga | 1860 |
| gcagaacacg gctgctatca ccagacaatt tcccaggatc accagcaaat cgatggtcag | 1920 |
| caaaaccgtg agacttgcta aggaagaagg actcagccag tcgacatttt caatttgagg | 1980 |
| acattcagtc ccatcatggt tgtacaaagt tgtcgaattt ccctgtcctg tggtaatggt | 2040 |
| tgccccagat aaggaagtcc cataacttag cctgattgtt gt | 2082 |

<210> SEQ ID NO 11
<211> LENGTH: 2136
<212> TYPE: DNA
<213> ORGANISM: Ctenocephalides felis
<220> FEATURE:
<221> NAME/KEY: CDS
<222> LOCATION: (1)..(2136)

<400> SEQUENCE: 11

| | |
|---|---|
| atg aat gcc tcg gag tac att aac acg aca aca atc agg cta agt tat<br>Met Asn Ala Ser Glu Tyr Ile Asn Thr Thr Thr Ile Arg Leu Ser Tyr<br>1               5                 10              15 | 48 |
| ggg act tcc tta tct ggg gca acc att acc aca gga cag gga aat tcg<br>Gly Thr Ser Leu Ser Gly Ala Thr Ile Thr Thr Gly Gln Gly Asn Ser<br>             20                 25                 30 | 96 |
| aca act ttg tac aac cat gat ggg act gaa tgt cct caa att gaa aat<br>Thr Thr Leu Tyr Asn His Asp Gly Thr Glu Cys Pro Gln Ile Glu Asn<br>        35                 40                 45 | 144 |
| gtc gac tgg ctg agt cct tct tcc tta gca agt ctc acg gtt ttg ctg<br>Val Asp Trp Leu Ser Pro Ser Ser Leu Ala Ser Leu Thr Val Leu Leu<br>50                55                 60 | 192 |

```
acc atc gat ttg ctg gtg atc ctg gga aat tgt ctg gtg ata gca gcc         240
Thr Ile Asp Leu Leu Val Ile Leu Gly Asn Cys Leu Val Ile Ala Ala
 65                  70                  75                  80 gtg ttc tgc tcc agc aaa ctg cgc agt gtg acc aac ttg ttc ata gtg         288
Val Phe Cys Ser Ser Lys Leu Arg Ser Val Thr Asn Leu Phe Ile Val
                 85                  90                  95 tca ctt gca gtc gcc gat ttg atg gtc ggc atc gcg gtt ttg cct ttt         336
Ser Leu Ala Val Ala Asp Leu Met Val Gly Ile Ala Val Leu Pro Phe
            100                 105                 110 agc gca act tgg gaa gtc ttc aag gtt tgg ata ttc gga agc agc tgg         384
Ser Ala Thr Trp Glu Val Phe Lys Val Trp Ile Phe Gly Ser Ser Trp
        115                 120                 125 tgc cga gcc tgg tta gcc ctg gac gtg tgg atg tgc aca gct tcg ata         432
Cys Arg Ala Trp Leu Ala Leu Asp Val Trp Met Cys Thr Ala Ser Ile
130                 135                 140 tta aat ctg tgc gca ata tcc ttg gat aga tat gtc gct gtc acc agg         480
Leu Asn Leu Cys Ala Ile Ser Leu Asp Arg Tyr Val Ala Val Thr Arg
145                 150                 155                 160 cca gtt gct tat ccg agc atc atg tct acg aaa agg gct aag gga ctc         528
Pro Val Ala Tyr Pro Ser Ile Met Ser Thr Lys Arg Ala Lys Gly Leu
                165                 170                 175 ata gcc ggg ctt tgg gtt ctt agt ttt gtg ata tgt ttt cca cct tta         576
Ile Ala Gly Leu Trp Val Leu Ser Phe Val Ile Cys Phe Pro Pro Leu
            180                 185                 190 gtc gga tgg aag gat aaa aag gaa tcc gag gat ctg ata gac ata tct         624
Val Gly Trp Lys Asp Lys Lys Glu Ser Glu Asp Leu Ile Asp Ile Ser
        195                 200                 205 tca tgt ccg tgg acg tgc gag ttg acg aat gat gca gga tat gtg gtg         672
Ser Cys Pro Trp Thr Cys Glu Leu Thr Asn Asp Ala Gly Tyr Val Val
210                 215                 220 tat tct gct cta gga tca ttc tac att cct atg ttt gtc atg tta ttt         720
Tyr Ser Ala Leu Gly Ser Phe Tyr Ile Pro Met Phe Val Met Leu Phe
225                 230                 235                 240 ttc tac tgg agg ata tat aga gca gct gtc agg aca acc aga gct atc         768
Phe Tyr Trp Arg Ile Tyr Arg Ala Ala Val Arg Thr Thr Arg Ala Ile
                245                 250                 255 aac caa gga ttc agg acc aca aaa ggt tcg cgt ggt ata gga cga ttt         816
Asn Gln Gly Phe Arg Thr Thr Lys Gly Ser Arg Gly Ile Gly Arg Phe
            260                 265                 270 gac gaa caa cgc cta act tta agg att cat aga gga cgg ggt ggt tct         864
Asp Glu Gln Arg Leu Thr Leu Arg Ile His Arg Gly Arg Gly Gly Ser
        275                 280                 285 gaa aat aga aga tgt cat cat cat tct tcc att aaa agc aat gct tca         912
Glu Asn Arg Arg Cys His His His Ser Ser Ile Lys Ser Asn Ala Ser
290                 295                 300 ggg aga atg tct aca tct act tct atg agg aat tgt tct cca caa cat         960
Gly Arg Met Ser Thr Ser Thr Ser Met Arg Asn Cys Ser Pro Gln His
305                 310                 315                 320 agt tca cca cgt agt gca agt acc agc tta gga agt act cac gaa tca        1008
Ser Ser Pro Arg Ser Ala Ser Thr Ser Leu Gly Ser Thr His Glu Ser
                325                 330                 335 cct gaa aaa tca tct ata tca agg acc aac acc tgg gtt tgc cat cat        1056
Pro Glu Lys Ser Ser Ile Ser Arg Thr Asn Thr Trp Val Leu His His
            340                 345                 350 gcg acc aat aat tcc aat tct gga gct tgt aac caa gta gtt atc gcc        1104
Ala Thr Asn Asn Ser Asn Ser Gly Ala Cys Asn Gln Val Val Ile Ala
        355                 360                 365 aat aat aca agt caa agt gca cca aac aat cag tta aat agt agt gcc        1152
Asn Asn Thr Ser Gln Ser Ala Pro Asn Asn Gln Leu Asn Ser Ser Ala
370                 375                 380
```

```
cag cct gaa gtc act gta aca aaa agt agt cga aga tct tcg aaa tca        1200
Gln Pro Glu Val Thr Val Thr Lys Ser Ser Arg Arg Ser Ser Lys Ser
385                 390                 395                 400 tat aag agc ttt aag aag gaa aga gtt caa att tcg gtg cag tat cca        1248
Tyr Lys Ser Phe Lys Lys Glu Arg Val Gln Ile Ser Val Gln Tyr Pro
                405                 410                 415 agt gca gaa aga ctt gat gaa ttg gaa ggt gaa tta gaa ggt gat gct        1296
Ser Ala Glu Arg Leu Asp Glu Leu Glu Gly Glu Leu Glu Gly Asp Ala
            420                 425                 430 aca aac aac atg tac acc gtc cac tac tct gtg tcc aat ggt aac agc        1344
Thr Asn Asn Met Tyr Thr Val His Tyr Ser Val Ser Asn Gly Asn Ser
        435                 440                 445 ttg tca aat cat tcg ttg atg cca gag cag caa ata gtc gat tct tcg        1392
Leu Ser Asn His Ser Leu Met Pro Glu Gln Gln Ile Val Asp Ser Ser
    450                 455                 460 agc caa caa cag acc att aag caa caa caa caa tta acg gtg aat cag        1440
Ser Gln Gln Gln Thr Ile Lys Gln Gln Gln Gln Leu Thr Val Asn Gln
465                 470                 475                 480 caa tta aat tcg ggt tcc atc tat cgg cca cag gat aat cat cat ctc        1488
Gln Leu Asn Ser Gly Ser Ile Tyr Arg Pro Gln Asp Asn His His Leu
                485                 490                 495 cga gtt acg tcg caa aga ttg gca ccg tcg cct aca ctg tcg aag gga        1536
Arg Val Thr Ser Gln Arg Leu Ala Pro Ser Pro Thr Leu Ser Lys Gly
            500                 505                 510 atg cat agg cga tcc agc agc tgc gat agt aga gat ttg gct ggg ttt        1584
Met His Arg Arg Ser Ser Ser Cys Asp Ser Arg Asp Leu Ala Gly Phe
        515                 520                 525 caa tta tgc gaa agt tca agt cca agt cca aca aga agg ata atg tct        1632
Gln Leu Cys Glu Ser Ser Ser Pro Ser Pro Thr Arg Arg Ile Met Ser
    530                 535                 540 gga agt ctt tat cgt gat gat agc gag tta ggt tcg act tcc aaa ctg        1680
Gly Ser Leu Tyr Arg Asp Asp Ser Glu Leu Gly Ser Thr Ser Lys Leu
545                 550                 555                 560 cag cag caa aat aga aaa atg ggc aaa cgt aat ata aaa gct cag gtg        1728
Gln Gln Gln Asn Arg Lys Met Gly Lys Arg Asn Ile Lys Ala Gln Val
                565                 570                 575 aaa cgg ttt cga atg gag acg aaa gct gcc aaa aca ctt gca ata att        1776
Lys Arg Phe Arg Met Glu Thr Lys Ala Ala Lys Thr Leu Ala Ile Ile
            580                 585                 590 gtc ggt ggt ttt att gta tgc tgg ttt ccc ttt ttc aca atg tac gta        1824
Val Gly Gly Phe Ile Val Cys Trp Phe Pro Phe Phe Thr Met Tyr Val
        595                 600                 605 ata aga gca ttt tgt cca gac tgc att cat cct gtt ctc ttc tcg gtt        1872
Ile Arg Ala Phe Cys Pro Asp Cys Ile His Pro Val Leu Phe Ser Val
    610                 615                 620 cta ttc tgg ctc ggc tac tgc aat tct gcc atc aat ccg ctg att tat        1920
Leu Phe Trp Leu Gly Tyr Cys Asn Ser Ala Ile Asn Pro Leu Ile Tyr
625                 630                 635                 640 gca ctt ttt agc aaa gat ttt aga tac gcc ttc aag cgc atc att tgc        1968
Ala Leu Phe Ser Lys Asp Phe Arg Tyr Ala Phe Lys Arg Ile Ile Cys
                645                 650                 655 aga tac tgc ttt tgt tgc ggt aat cgt acc gag gcc cag cac agc ggt        2016
Arg Tyr Cys Phe Cys Cys Gly Asn Arg Thr Glu Ala Gln His Ser Gly
            660                 665                 670 gga gct ggt ggt tct aga aga ggg tcc gat gga tct caa atg aaa act        2064
Gly Ala Gly Gly Ser Arg Arg Gly Ser Asp Gly Ser Gln Met Lys Thr
        675                 680                 685 aat ttt agg ttt aat acc agt ttt aat acc aaa aac tgc gtt cgt caa        2112
Asn Phe Arg Phe Asn Thr Ser Phe Asn Thr Lys Asn Cys Val Arg Gln
    690                 695                 700
```

```
gat agt gat aat gat gtc aca aga                                    2136
Asp Ser Asp Asn Asp Val Thr Arg
705             710
```

<210> SEQ ID NO 12
<211> LENGTH: 712
<212> TYPE: PRT
<213> ORGANISM: Ctenocephalides felis

<400> SEQUENCE: 12

```
Met Asn Ala Ser Glu Tyr Ile Asn Thr Thr Ile Arg Leu Ser Tyr
1               5                   10                  15

Gly Thr Ser Leu Ser Gly Ala Thr Ile Thr Thr Gly Gln Gly Asn Ser
            20                  25                  30

Thr Thr Leu Tyr Asn His Asp Gly Thr Glu Cys Pro Gln Ile Glu Asn
            35                  40                  45

Val Asp Trp Leu Ser Pro Ser Ser Leu Ala Ser Leu Thr Val Leu Leu
    50                  55                  60

Thr Ile Asp Leu Leu Val Ile Leu Gly Asn Cys Leu Val Ile Ala Ala
65                  70                  75                  80

Val Phe Cys Ser Ser Lys Leu Arg Ser Val Thr Asn Leu Phe Ile Val
                85                  90                  95

Ser Leu Ala Val Ala Asp Leu Met Val Gly Ile Ala Val Leu Pro Phe
            100                 105                 110

Ser Ala Thr Trp Glu Val Phe Lys Val Trp Ile Phe Gly Ser Ser Trp
        115                 120                 125

Cys Arg Ala Trp Leu Ala Leu Asp Val Trp Met Cys Thr Ala Ser Ile
130                 135                 140

Leu Asn Leu Cys Ala Ile Ser Leu Asp Arg Tyr Val Ala Val Thr Arg
145                 150                 155                 160

Pro Val Ala Tyr Pro Ser Ile Met Ser Thr Lys Arg Ala Lys Gly Leu
                165                 170                 175

Ile Ala Gly Leu Trp Val Leu Ser Phe Val Ile Cys Phe Pro Pro Leu
            180                 185                 190

Val Gly Trp Lys Asp Lys Lys Glu Ser Glu Asp Leu Ile Asp Ile Ser
        195                 200                 205

Ser Cys Pro Trp Thr Cys Glu Leu Thr Asn Asp Ala Gly Tyr Val Val
210                 215                 220

Tyr Ser Ala Leu Gly Ser Phe Tyr Ile Pro Met Phe Val Met Leu Phe
225                 230                 235                 240

Phe Tyr Trp Arg Ile Tyr Arg Ala Ala Val Arg Thr Thr Arg Ala Ile
                245                 250                 255

Asn Gln Gly Phe Arg Thr Thr Lys Gly Ser Arg Gly Ile Gly Arg Phe
            260                 265                 270

Asp Glu Gln Arg Leu Thr Leu Arg Ile His Arg Gly Arg Gly Gly Ser
        275                 280                 285

Glu Asn Arg Arg Cys His His His Ser Ser Ile Lys Ser Asn Ala Ser
290                 295                 300

Gly Arg Met Ser Thr Ser Thr Ser Met Arg Asn Cys Ser Pro Gln His
305                 310                 315                 320

Ser Ser Pro Arg Ser Ala Ser Thr Ser Leu Gly Ser Thr His Glu Ser
                325                 330                 335

Pro Glu Lys Ser Ser Ile Ser Arg Thr Asn Thr Trp Val Leu His His
            340                 345                 350

Ala Thr Asn Asn Ser Asn Ser Gly Ala Cys Asn Gln Val Val Ile Ala
```

```
                355                 360                 365
Asn Asn Thr Ser Gln Ser Ala Pro Asn Gln Leu Asn Ser Ser Ala
        370                 375                 380
Gln Pro Glu Val Thr Val Thr Lys Ser Arg Arg Ser Ser Lys Ser
385                 390                 395                 400
Tyr Lys Ser Phe Lys Lys Glu Arg Val Gln Ile Ser Val Gln Tyr Pro
                405                 410                 415
Ser Ala Glu Arg Leu Asp Glu Leu Gly Glu Leu Glu Gly Asp Ala
        420                 425                 430
Thr Asn Asn Met Tyr Thr Val His Tyr Ser Val Ser Asn Gly Asn Ser
                435                 440                 445
Leu Ser Asn His Ser Leu Met Pro Glu Gln Gln Ile Val Asp Ser Ser
        450                 455                 460
Ser Gln Gln Gln Thr Ile Lys Gln Gln Gln Leu Thr Val Asn Gln
465                 470                 475                 480
Gln Leu Asn Ser Gly Ser Ile Tyr Arg Pro Gln Asp Asn His His Leu
                485                 490                 495
Arg Val Thr Ser Gln Arg Leu Ala Pro Ser Pro Thr Leu Ser Lys Gly
                500                 505                 510
Met His Arg Arg Ser Ser Ser Cys Asp Ser Arg Asp Leu Ala Gly Phe
        515                 520                 525
Gln Leu Cys Glu Ser Ser Ser Pro Ser Pro Thr Arg Arg Ile Met Ser
        530                 535                 540
Gly Ser Leu Tyr Arg Asp Asp Ser Glu Leu Gly Ser Thr Ser Lys Leu
545                 550                 555                 560
Gln Gln Gln Asn Arg Lys Met Gly Lys Arg Asn Ile Lys Ala Gln Val
                565                 570                 575
Lys Arg Phe Arg Met Glu Thr Lys Ala Ala Lys Thr Leu Ala Ile Ile
                580                 585                 590
Val Gly Gly Phe Ile Val Cys Trp Phe Pro Phe Phe Thr Met Tyr Val
        595                 600                 605
Ile Arg Ala Phe Cys Pro Asp Cys Ile His Pro Val Leu Phe Ser Val
610                 615                 620
Leu Phe Trp Leu Gly Tyr Cys Asn Ser Ala Ile Asn Pro Leu Ile Tyr
625                 630                 635                 640
Ala Leu Phe Ser Lys Asp Phe Arg Tyr Ala Phe Lys Arg Ile Ile Cys
                645                 650                 655
Arg Tyr Cys Phe Cys Cys Gly Asn Arg Thr Glu Ala Gln His Ser Gly
                660                 665                 670
Gly Ala Gly Gly Ser Arg Arg Gly Ser Asp Gly Ser Gln Met Lys Thr
        675                 680                 685
Asn Phe Arg Phe Asn Thr Ser Phe Asn Thr Lys Asn Cys Val Arg Gln
        690                 695                 700
Asp Ser Asp Asn Asp Val Thr Arg
705                 710

<210> SEQ ID NO 13
<211> LENGTH: 2136
<212> TYPE: DNA
<213> ORGANISM: Ctenocephalides felis

<400> SEQUENCE: 13
tcttgtgaca tcattatcac tatcttgacg aacgcagttt ttggtattaa aactggtatt     60
aaacctaaaa ttagttttca tttgagatcc atcggaccct cttctagaac caccagctcc    120
```

```
accgctgtgc tgggcctcgg tacgattacc gcaacaaaag cagtatctgc aaatgatgcg      180
cttgaaggcg tatctaaaat ctttgctaaa aagtgcataa atcagcggat tgatggcaga      240
attgcagtag ccgagccaga atagaaccga gaagagaaca ggatgaatgc agtctggaca      300
aaatgctctt attacgtaca ttgtgaaaaa gggaaaccag catacaataa aaccaccgac      360
aattattgca agtgttttgg cagctttcgt ctccattcga aaccgtttca cctgagcttt      420
tatattacgt ttgcccattt ttctattttg ctgctgcagt ttggaagtcg aacctaactc      480
gctatcatca cgataaagac ttccagacat tatccttctt gttggacttg gacttgaact      540
ttcgcataat tgaaacccag ccaaatctct actatcgcag ctgctggatc gcctatgcat      600
tcccttcgac agtgtaggcg acggtgccaa tctttgcgac gtaactcgga gatgatgatt      660
atcctgtggc cgatagatgg aacccgaatt taattgctga ttcaccgtta attgttgttg      720
ttgcttaatg gtctgttgtt ggctcgaaga atcgactatt tgctgctctg gcatcaacga      780
atgatttgac aagctgttac cattggacac agagtagtgg acggtgtaca tgttgtttgt      840
agcatcacct tctaattcac cttccaattc atcaagtctt tctgcacttg gatactgcac      900
cgaaatttga actctttcct tcttaaagct cttatatgat ttcgaagatc ttcgactact      960
ttttgttaca gtgacttcag gctgggcact actatttaac tgattgtttg gtgcactttg     1020
acttgtatta ttggcgataa ctacttggtt acaagctcca gaattggaat tattggtcgc     1080
atgatgcaaa acccaggtgt tggtccttga tatagatgat ttttcaggtg attcgtgagt     1140
acttcctaag ctggtacttg cactacgtgg tgaactatgt tgtggagaac aattcctcat     1200
agaagtagat gtagacattc tccctgaagc attgcttttta atggaagaat gatgatgaca     1260
tcttctattt tcagaaccac cccgtcctct atgaatcctt aaagttaggc gttgttcgtc     1320
aaatcgtcct ataccacgcg aacctttgt ggtcctgaat ccttggttga tagctctggt      1380
tgtcctgaca gctgctctat atatcctcca gtagaaaaat aacatgacaa acataggaat     1440
gtagaatgat cctagagcag aatacaccac atatcctgca tcattcgtca actcgcacgt     1500
ccacggacat gaagatatgt ctatcagatc ctcggattcc tttttatcct tccatccgac     1560
taaaggtgga aaacatatca caaaactaag aacccaaagc ccggctatga gtcccttagc     1620
ccttttcgta gacatgatgc tcggataagc aactggcctg gtgacagcga catatctatc     1680
caaggatatt gcgcacagat ttaatatcga agctgtgcac atccacacgt ccagggctaa     1740
ccaggctcgg caccagctgc ttccgaatat ccaaaccttg aagacttccc aagttgcgct     1800
aaaaggcaaa accgcgatgc cgaccatcaa atcggcgact gcaagtgaca ctatgaacaa     1860
gttggtcaca ctgcgcagtt tgctggagca gaacacggct gctatcacca gacaatttcc     1920
caggatcacc agcaaatcga tggtcagcaa accgtgaga cttgctaagg aagaaggact      1980
cagccagtcg acattttcaa tttgaggaca ttcagtccca tcatggttgt acaaagttgt     2040
cgaatttccc tgtcctgtgg taatggttgc cccagataag gaagtcccat aacttagcct     2100
gattgttgtc gtgttaatgt actccgaggc attcat                               2136
```

<210> SEQ ID NO 14
<211> LENGTH: 20
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (3)..(3)
<223> OTHER INFORMATION: n = unknown
<220> FEATURE:

```
<221> NAME/KEY: misc_feature
<222> LOCATION: (9)..(9)
<223> OTHER INFORMATION: n = unknown

<400> SEQUENCE: 14
gtngaygtnt ggatgtgyac                                              20

<210> SEQ ID NO 15
<211> LENGTH: 18
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (4)..(4)
<223> OTHER INFORMATION: n = unknown
<220> FEATURE:
<221> NAME/KEY: misc_feature
<222> LOCATION: (16)..(16)
<223> OTHER INFORMATION: n = unknown

<400> SEQUENCE: 15
tggnggraar cadatnac                                                18

<210> SEQ ID NO 16
<211> LENGTH: 22
<212> TYPE: DNA
<213> ORGANISM: Artificial
<220> FEATURE:
<223> OTHER INFORMATION: Synthetic Primer

<400> SEQUENCE: 16
atgtgtggat gtgtacagct tc                                           22

<210> SEQ ID NO 17
<211> LENGTH: 22
<212> TYPE: DNA
<213> ORGANISM: Artificial
<220> FEATURE:
<223> OTHER INFORMATION: Synthetic Primer

<400> SEQUENCE: 17
gtaatacgac tcactatagg gc                                           22

<210> SEQ ID NO 18
<211> LENGTH: 23
<212> TYPE: DNA
<213> ORGANISM: Artificial
<220> FEATURE:
<223> OTHER INFORMATION: Synthetic Primer

<400> SEQUENCE: 18
aaatctgtgc gcaatatcct tgg                                          23

<210> SEQ ID NO 19
<211> LENGTH: 27
<212> TYPE: DNA
<213> ORGANISM: Artificial
<220> FEATURE:
<223> OTHER INFORMATION: Synthetic Primer

<400> SEQUENCE: 19
ccatcctaat acgactcact atagggc                                      27

<210> SEQ ID NO 20
<211> LENGTH: 22
<212> TYPE: DNA
```

```
<213> ORGANISM: Artificial
<220> FEATURE:
<223> OTHER INFORMATION: Synthetic Primer

<400> SEQUENCE: 20
ggaagcagat cacaaaacta ag                                              22

<210> SEQ ID NO 21
<211> LENGTH: 22
<212> TYPE: DNA
<213> ORGANISM: Artificial
<220> FEATURE:
<223> OTHER INFORMATION: Synthetic Primer

<400> SEQUENCE: 21
ccaaagcccg gctatgagtc cc                                              22

<210> SEQ ID NO 22
<211> LENGTH: 38
<212> TYPE: DNA
<213> ORGANISM: Artificial
<220> FEATURE:
<223> OTHER INFORMATION: Synthetic Primer

<400> SEQUENCE: 22
aagaattcga tatgaatgcc tcggagtaca ttaacacg                             38

<210> SEQ ID NO 23
<211> LENGTH: 37
<212> TYPE: DNA
<213> ORGANISM: Artificial
<220> FEATURE:
<223> OTHER INFORMATION: Synthetic Primer

<400> SEQUENCE: 23
ttctcgagcc tcttgtgaca tcattatcac tatcttg                              37

<210> SEQ ID NO 24
<211> LENGTH: 36
<212> TYPE: DNA
<213> ORGANISM: Artificial
<220> FEATURE:
<223> OTHER INFORMATION: Synthetic Primer

<400> SEQUENCE: 24
cagagctatc aaccaaggat tcaggaccac aaaagg                               36

<210> SEQ ID NO 25
<211> LENGTH: 21
<212> TYPE: DNA
<213> ORGANISM: Artificial
<220> FEATURE:
<223> OTHER INFORMATION: Synthetic Primer

<400> SEQUENCE: 25
cttggtaccg agctcggatc c                                               21

<210> SEQ ID NO 26
<211> LENGTH: 36
<212> TYPE: DNA
<213> ORGANISM: Artificial
<220> FEATURE:
<223> OTHER INFORMATION: Synthetic Primer

<400> SEQUENCE: 26 cctttttgtgg tcctgaatcc ttggttgata gctctg                              36
```

<210> SEQ ID NO 27
<211> LENGTH: 21
<212> TYPE: DNA
<213> ORGANISM: Artificial
<220> FEATURE:
<223> OTHER INFORMATION: Synthetic Primer

<400> SEQUENCE: 27
agatgcatgc tcgagcggcc g                                          21

<210> SEQ ID NO 28
<211> LENGTH: 38
<212> TYPE: DNA
<213> ORGANISM: Artificial
<220> FEATURE:
<223> OTHER INFORMATION: Synthetic Primer

<400> SEQUENCE: 28
atgaatgcct cggagtacat taacacgaca acaatcag                        38

<210> SEQ ID NO 29
<211> LENGTH: 37
<212> TYPE: DNA
<213> ORGANISM: Artificial
<220> FEATURE:
<223> OTHER INFORMATION: Synthetic Primer

<400> SEQUENCE: 29
tcatcttgtg acatcattat cactatcttg acgaacg                         37

<210> SEQ ID NO 30
<211> LENGTH: 102
<212> TYPE: DNA
<213> ORGANISM: Rhipicephalus saguineus
<220> FEATURE:
<221> NAME/KEY: CDS
<222> LOCATION: (1)..(102)

<400> SEQUENCE: 30 gcc atc att gtg ggc atc ttc atc gtg tgc tgg att aca gtg cat acc     48
Ala Ile Ile Val Gly Ile Phe Ile Val Cys Trp Ile Thr Val His Thr
1               5                   10                  15 ttt aga ttc ttt aag caa aca ctt ggc tac tgc aac tcg gcc ata aac     96
Phe Arg Phe Phe Lys Gln Thr Leu Gly Tyr Cys Asn Ser Ala Ile Asn
                20                  25                  30 ccc aga                                                            102
Pro Arg

<210> SEQ ID NO 31
<211> LENGTH: 34
<212> TYPE: PRT
<213> ORGANISM: Rhipicephalus saguineus

<400> SEQUENCE: 31

Ala Ile Ile Val Gly Ile Phe Ile Val Cys Trp Ile Thr Val His Thr
1               5                   10                  15

Phe Arg Phe Phe Lys Gln Thr Leu Gly Tyr Cys Asn Ser Ala Ile Asn
                20                  25                  30

Pro Arg

<210> SEQ ID NO 32
<211> LENGTH: 102
<212> TYPE: DNA
<213> ORGANISM: Rhipicephalus saguineus -continued

```
<400> SEQUENCE: 32
tctggggttt atggccgagt tgcagtagcc aagtgtttgc ttaaagaatc taaaggtatg      60
cactgtaatc cagcacacga tgaagatgcc acaatgatg gc                         102

<210> SEQ ID NO 33
<211> LENGTH: 499
<212> TYPE: DNA
<213> ORGANISM: Rhipicephalus saguineus
<220> FEATURE:
<221> NAME/KEY: CDS
<222> LOCATION: (3)..(278)
<220> FEATURE:
<221> NAME/KEY: misc_feature
<222> LOCATION: (8)..(8)
<223> OTHER INFORMATION: n = unknown
      Xaa at location 2 = Tyr

<400> SEQUENCE: 33 tg tct tan gag tca tca ccg tgg cat tcg ccc ttg gtg cgt gca ttc        47
   Ser Xaa Glu Ser Ser Pro Trp His Ser Pro Leu Val Arg Ala Phe
   1               5                   10                  15 tgc gag cac tgc atc ccc aac ctg ctg ttc tcg gtc ttc ttc tgg ctc       95
Cys Glu His Cys Ile Pro Asn Leu Leu Phe Ser Val Phe Phe Trp Leu
                20                  25                  30 gga tac tgc aac tcg gcc atc aac ccg ctc atc tac gtg ctt gtc agc      143
Gly Tyr Cys Asn Ser Ala Ile Asn Pro Leu Ile Tyr Val Leu Val Ser
            35                  40                  45 aag gac ttt cgg ctg gcc ttc aag cgc atc ctg tgt cgc tgc cgc ctc      191
Lys Asp Phe Arg Leu Ala Phe Lys Arg Ile Leu Cys Arg Cys Arg Leu
        50                  55                  60 aaa gaa gga ggc gtc tcg tca ctc atc aaa cag atc cac atg ctc acc      239
Lys Glu Gly Gly Val Ser Ser Leu Ile Lys Gln Ile His Met Leu Thr
65                  70                  75                  80 gta ctt gac gac gca ccc ccg gac aac gcc gag tcg ccc tagaatcctg       288
Val Leu Asp Asp Ala Pro Pro Asp Asn Ala Glu Ser Pro
                85                  90 gtcacagcct tctcctgccc gcgctatcgc ggcattctca tggggcgcca ctgcttcttt    348
gcacctcacc cgctcactgc accgcgtgtc tctgccgtag tgacattgtc ggtgtccatc    408
tcacggctgt aatgtctcct tcctcaccca cgtgaatcac cactatagcc acagagcaaa    468
cgtgccagta ccaagagcgc ttctgccgca c                                   499

<210> SEQ ID NO 34
<211> LENGTH: 92
<212> TYPE: PRT
<213> ORGANISM: Rhipicephalus saguineus
<220> FEATURE:
<221> NAME/KEY: misc_feature
<222> LOCATION: (2)..(2)
<223> OTHER INFORMATION: The 'Xaa' at location 2 stands for Tyr.

<400> SEQUENCE: 34

Ser Xaa Glu Ser Ser Pro Trp His Ser Pro Leu Val Arg Ala Phe Cys
1               5                   10                  15

Glu His Cys Ile Pro Asn Leu Leu Phe Ser Val Phe Phe Trp Leu Gly
            20                  25                  30

Tyr Cys Asn Ser Ala Ile Asn Pro Leu Ile Tyr Val Leu Val Ser Lys
        35                  40                  45

Asp Phe Arg Leu Ala Phe Lys Arg Ile Leu Cys Arg Cys Arg Leu Lys
    50                  55                  60

Glu Gly Gly Val Ser Ser Leu Ile Lys Gln Ile His Met Leu Thr Val
65                  70                  75                  80
```

```
<210> SEQ ID NO 35
<211> LENGTH: 499
<212> TYPE: DNA
<213> ORGANISM: Rhipicephalus saguineus
<220> FEATURE:
<221> NAME/KEY: misc_feature
<222> LOCATION: (492)..(492)
<223> OTHER INFORMATION: n = unknown

<400> SEQUENCE: 35
gtgcggcaga agcgctcttg gtactggcac gtttgctctg tggctatagt ggtgattcac      60
gtgggtgagg aaggagacat tacagccgtg agatggacac cgacaatgtc actacggcag     120
agacacgcgg tgcagtgagc gggtgaggtg caaagaagca gtggcgcccc atgagaatgc     180
cgcgatagcg cgggcaggag aaggctgtga ccaggattct agggcgactc ggcgttgtcc     240
gggggtgcgt cgtcaagtac ggtgagcatg tggatctgtt tgatgagtga cgagacgcct     300
ccttctttga ggcggcagcg acacaggatg cgcttgaagg ccagccgaaa gtccttgctg     360
acaagcacgt agatgagcgg gttgatggcc gagttgcagt atccgagcca aagaagacc      420
gagaacagca ggttggggat gcagtgctcg cagaatgcac gcaccaaggg cgaatgccac     480
ggtgatgact cntaagaca                                                  499

<210> SEQ ID NO 36
<211> LENGTH: 286
<212> TYPE: DNA
<213> ORGANISM: Rhipicephalus saguineus
<220> FEATURE:
<221> NAME/KEY: CDS
<222> LOCATION: (1)..(285)

<400> SEQUENCE: 36 cgg ccc ggt agc aac atg aac gag acg tgc ctg tcc cgc gtg ccg cca       48
Arg Pro Gly Ser Asn Met Asn Glu Thr Cys Leu Ser Arg Val Pro Pro
 1               5                  10                  15 gag aag ctc cat gag ccg gtc act gtg gcc ctg ttc ttc gta ctg ggc       96
Glu Lys Leu His Glu Pro Val Thr Val Ala Leu Phe Phe Val Leu Gly
             20                  25                  30 tcc atc aat gga ctc gtc atc ttc ggt aac ctg ctg gtc att atc gcc      144
Ser Ile Asn Gly Leu Val Ile Phe Gly Asn Leu Leu Val Ile Ile Ala
         35                  40                  45 gtg ctg gcc tca aca aag ctg cgc acg gtc acc aac tac ttc gtg gtg      192
Val Leu Ala Ser Thr Lys Leu Arg Thr Val Thr Asn Tyr Phe Val Val
     50                  55                  60 tcc ttg gct gtg gcc gac ctc tcg gtt ggg ctc acc gtg ttg cca tac      240
Ser Leu Ala Val Ala Asp Leu Ser Val Gly Leu Thr Val Leu Pro Tyr
 65                  70                  75                  80 tca att gtg ttg gag gtg ctc gag gtg tgg ctc ttc ggc caa cct g        286
Ser Ile Val Leu Glu Val Leu Glu Val Trp Leu Phe Gly Gln Pro
                 85                  90                  95

<210> SEQ ID NO 37
<211> LENGTH: 95
<212> TYPE: PRT
<213> ORGANISM: Rhipicephalus saguineus

<400> SEQUENCE: 37

Arg Pro Gly Ser Asn Met Asn Glu Thr Cys Leu Ser Arg Val Pro Pro
 1               5                  10                  15
```

Leu Asp Asp Ala Pro Pro Asp Asn Ala Glu Ser Pro
                85                  90

```
Glu Lys Leu His Glu Pro Val Thr Val Ala Leu Phe Phe Val Leu Gly
         20                  25                  30

Ser Ile Asn Gly Leu Val Ile Phe Gly Asn Leu Leu Val Ile Ile Ala
         35                  40                  45

Val Leu Ala Ser Thr Lys Leu Arg Thr Val Thr Asn Tyr Phe Val Val
 50                  55                  60

Ser Leu Ala Val Ala Asp Leu Ser Val Gly Leu Thr Val Leu Pro Tyr
 65                  70                  75                  80

Ser Ile Val Leu Glu Val Leu Glu Val Trp Leu Phe Gly Gln Pro
             85                  90                  95

<210> SEQ ID NO 38
<211> LENGTH: 286
<212> TYPE: DNA
<213> ORGANISM: Rhipicephalus saguineus

<400> SEQUENCE: 38
caggttggcc gaagagccac acctcgagca cctccaacac aattgagtat ggcaacacgg    60
tgagcccaac cgagaggtcg gccacagcca aggacaccac gaagtagttg gtgaccgtgc   120
gcagctttgt tgaggccagc acggcgataa tgaccagcag gttaccgaag atgacgagtc   180
cattgatgga gcccagtacg aagaacaggg ccacagtgac cggctcatgg agcttctctg   240
gcggcacgcg ggacaggcac gtctcgttca tgttgctacc gggccg                  286

<210> SEQ ID NO 39
<211> LENGTH: 1443
<212> TYPE: DNA
<213> ORGANISM: Rhipicephalus sanguineus
<220> FEATURE:
<221> NAME/KEY: CDS
<222> LOCATION: (1)..(1440)

<400> SEQUENCE: 39 atg aac gag acg tgc ctg tcc cgc gtg ccg cca gag aag ctc cat gag    48
Met Asn Glu Thr Cys Leu Ser Arg Val Pro Pro Glu Lys Leu His Glu
 1               5                  10                  15 ccg gtc act gtg gcc ctg ttc ttc gta ctg ggc tcc atc aat gga ctc    96
Pro Val Thr Val Ala Leu Phe Phe Val Leu Gly Ser Ile Asn Gly Leu
                 20                  25                  30 gtc atc ttc ggt aac ctg ctg gtc att atc gcc gtg ctg gcc tca aca   144
Val Ile Phe Gly Asn Leu Leu Val Ile Ile Ala Val Leu Ala Ser Thr
             35                  40                  45 aag ctg cgc acg gtc acc aac tac ttc gtg gtg tcc ttg gct gtg gcc   192
Lys Leu Arg Thr Val Thr Asn Tyr Phe Val Val Ser Leu Ala Val Ala
         50                  55                  60 gac ctc tcg gtt ggg ctc acc gtg ttg cca tac tca att gtg ttg gag   240
Asp Leu Ser Val Gly Leu Thr Val Leu Pro Tyr Ser Ile Val Leu Glu
 65                  70                  75                  80 gtg ctc gag gtg tgg atc ttc ggc cac acc tgg tgc cag ata tgg cta   288
Val Leu Glu Val Trp Ile Phe Gly His Thr Trp Cys Gln Ile Trp Leu
                 85                  90                  95 gct gtg gac gta tgg ctc tgc aca tca tcc atc ctg aat ctc tgc gcc   336
Ala Val Asp Val Trp Leu Cys Thr Ser Ser Ile Leu Asn Leu Cys Ala
            100                 105                 110 atc agc gtg gac cgc tac ttg gcc atc acg cgg ccg gtt cgc tac cgg   384
Ile Ser Val Asp Arg Tyr Leu Ala Ile Thr Arg Pro Val Arg Tyr Arg
        115                 120                 125 agc ctc atg tcg tcg cgc cgc gcc aag ttg ctc atc gtg gcg gtg tgg   432
Ser Leu Met Ser Ser Arg Arg Ala Lys Leu Leu Ile Val Ala Val Trp
    130                 135                 140
```

| | | |
|---|---|---|
| gtg atc gcc ttt gtc atc tgc ttc ccg ccg ctc gtt gga tgg aac gac<br>Val Ile Ala Phe Val Ile Cys Phe Pro Pro Leu Val Gly Trp Asn Asp<br>145                    150                    155                    160 | 480 |
| ggc ggg tct caa aac agc gtg cct tac cac ggg tcg aac gag acc ttg<br>Gly Gly Ser Gln Asn Ser Val Pro Tyr His Gly Ser Asn Glu Thr Leu<br>                  165                    170                    175 | 528 |
| cac aat tcg agc atc gct gcc gat ggc ccg ttg ccg ctc tgc aag tcc<br>His Asn Ser Ser Ile Ala Ala Asp Gly Pro Leu Pro Leu Cys Lys Ser<br>            180                    185                    190 | 576 |
| gca caa tgt gtg ctg ata aac aac aag ggc tac gtc atc tac tcg gct<br>Ala Gln Cys Val Leu Ile Asn Asn Lys Gly Tyr Val Ile Tyr Ser Ala<br>195                    200                    205 | 624 |
| ctg ggc tct ttc tac ata ccg atg ctg ttc atg ctg ttt ttc aac tac<br>Leu Gly Ser Phe Tyr Ile Pro Met Leu Phe Met Leu Phe Phe Asn Tyr<br>            210                    215                    220 | 672 |
| cgc ata tac cgc gca gcc atc cag act ggg cgc gcc ctt gaa cga ggt<br>Arg Ile Tyr Arg Ala Ala Ile Gln Thr Gly Arg Ala Leu Glu Arg Gly<br>225                    230                    235                    240 | 720 |
| ttc ata acc aca aag tca gga aag atc aag gga cgc aca acg gac cag<br>Phe Ile Thr Thr Lys Ser Gly Lys Ile Lys Gly Arg Thr Thr Asp Gln<br>                  245                    250                    255 | 768 |
| agg ctc acg cta cgc gtc cac cgc ggt aac gat tcc gct atg aac gcc<br>Arg Leu Thr Leu Arg Val His Arg Gly Asn Asp Ser Ala Met Asn Ala<br>            260                    265                    270 | 816 |
| aag cga ggt agc gag cac ctc ggt gct gag acc tgc atc gat ggc atc<br>Lys Arg Gly Ser Glu His Leu Gly Ala Glu Thr Cys Ile Asp Gly Ile<br>275                    280                    285 | 864 |
| gtc acc ggt cgt cgc cgg ccc gga ctc aag aag tcg cgc gac gag ccg<br>Val Thr Gly Arg Arg Arg Pro Gly Leu Lys Lys Ser Arg Asp Glu Pro<br>            290                    295                    300 | 912 |
| tca gcc agc gcc cgg tcg tca gcc agc aag acg cgt cag caa agt gac<br>Ser Ala Ser Ala Arg Ser Ser Ala Ser Lys Thr Arg Gln Gln Ser Asp<br>305                    310                    315                    320 | 960 |
| cag cgg acc acg cgc tcg gcg ccg ccc tcg ttc aag tcg aac agg ggc<br>Gln Arg Thr Thr Arg Ser Ala Pro Pro Ser Phe Lys Ser Asn Arg Gly<br>                  325                    330                    335 | 1008 |
| agc gcc cgc aac agt gga cgc aac ggc act tcc acg tct agc ggc ggc<br>Ser Ala Arg Asn Ser Gly Arg Asn Gly Thr Ser Thr Ser Ser Gly Gly<br>            340                    345                    350 | 1056 |
| ggc aag ggc tcg cgt tcg agc aaa cgc agt caa cgg tgg cag gcc aag<br>Gly Lys Gly Ser Arg Ser Ser Lys Arg Ser Gln Arg Trp Gln Ala Lys<br>355                    360                    365 | 1104 |
| cga ttc cgc aca gag gcc aag gcc acc aag acc gtg ggc acc atc gtg<br>Arg Phe Arg Thr Glu Ala Lys Ala Thr Lys Thr Val Gly Thr Ile Val<br>            370                    375                    380 | 1152 |
| ggt ggc ttt ata tgc tgc tgg ctg ccc ttc ttc aca gtg tac ctg gtg<br>Gly Gly Phe Ile Cys Cys Trp Leu Pro Phe Phe Thr Val Tyr Leu Val<br>385                    390                    395                    400 | 1200 |
| cgt gca ttc tgc gag cac tgc atc ccc aac ctg ctg ttc tcg gtc ttc<br>Arg Ala Phe Cys Glu His Cys Ile Pro Asn Leu Leu Phe Ser Val Phe<br>                  405                    410                    415 | 1248 |
| ttc tgg ctc gga tac tgc aac tcg gcc atc aac ccg ctc atc tac gtg<br>Phe Trp Leu Gly Tyr Cys Asn Ser Ala Ile Asn Pro Leu Ile Tyr Val<br>            420                    425                    430 | 1296 |
| ctt gtc agc aag gac ttt cgg ctg gcc ttc aag cgc atc ctg tgt cgc<br>Leu Val Ser Lys Asp Phe Arg Leu Ala Phe Lys Arg Ile Leu Cys Arg<br>                  435                    440                    445 | 1344 |
| tgc cgc ctc aaa gaa gga ggc gtc tcg tca ctc atc aaa cag atc cac<br>Cys Arg Leu Lys Glu Gly Gly Val Ser Ser Leu Ile Lys Gln Ile His<br>        450                    455                    460 | 1392 |

```
atg ctc acc gta ctt gac gac gca ccc ccg gac aac gcc gag tcg ccc    1440
Met Leu Thr Val Leu Asp Asp Ala Pro Pro Asp Asn Ala Glu Ser Pro
465             470                 475                 480 tag                                                                1443
```

<210> SEQ ID NO 40
<211> LENGTH: 480
<212> TYPE: PRT
<213> ORGANISM: Rhipicephalus sanguineus

<400> SEQUENCE: 40

```
Met Asn Glu Thr Cys Leu Ser Arg Val Pro Pro Glu Lys Leu His Glu
1               5                   10                  15

Pro Val Thr Val Ala Leu Phe Phe Val Leu Gly Ser Ile Asn Gly Leu
            20                  25                  30

Val Ile Phe Gly Asn Leu Leu Val Ile Ala Val Leu Ala Ser Thr
        35                  40                  45

Lys Leu Arg Thr Val Thr Asn Tyr Phe Val Val Ser Leu Ala Val Ala
50                  55                  60

Asp Leu Ser Val Gly Leu Thr Val Leu Pro Tyr Ser Ile Val Leu Glu
65                  70                  75                  80

Val Leu Glu Val Trp Ile Phe Gly His Thr Trp Cys Gln Ile Trp Leu
                85                  90                  95

Ala Val Asp Val Trp Leu Cys Thr Ser Ser Ile Leu Asn Leu Cys Ala
            100                 105                 110

Ile Ser Val Asp Arg Tyr Leu Ala Ile Thr Arg Pro Val Arg Tyr Arg
        115                 120                 125

Ser Leu Met Ser Ser Arg Arg Ala Lys Leu Leu Ile Val Ala Val Trp
130                 135                 140

Val Ile Ala Phe Val Ile Cys Phe Pro Pro Leu Val Gly Trp Asn Asp
145                 150                 155                 160

Gly Gly Ser Gln Asn Ser Val Pro Tyr His Gly Ser Asn Glu Thr Leu
                165                 170                 175

His Asn Ser Ser Ile Ala Ala Asp Gly Pro Leu Pro Leu Cys Lys Ser
            180                 185                 190

Ala Gln Cys Val Leu Ile Asn Asn Lys Gly Tyr Val Ile Tyr Ser Ala
        195                 200                 205

Leu Gly Ser Phe Tyr Ile Pro Met Leu Phe Met Leu Phe Phe Asn Tyr
210                 215                 220

Arg Ile Tyr Arg Ala Ala Ile Gln Thr Gly Arg Ala Leu Glu Arg Gly
225                 230                 235                 240

Phe Ile Thr Thr Lys Ser Gly Lys Ile Lys Gly Arg Thr Thr Asp Gln
                245                 250                 255

Arg Leu Thr Leu Arg Val His Arg Gly Asn Asp Ser Ala Met Asn Ala
            260                 265                 270

Lys Arg Gly Ser Glu His Leu Gly Ala Glu Thr Cys Ile Asp Gly Ile
        275                 280                 285

Val Thr Gly Arg Arg Pro Gly Leu Lys Lys Ser Arg Asp Glu Pro
290                 295                 300

Ser Ala Ser Ala Arg Ser Ser Ala Ser Lys Thr Arg Gln Gln Ser Asp
305                 310                 315                 320

Gln Arg Thr Thr Arg Ser Ala Pro Pro Ser Phe Lys Ser Asn Arg Gly
                325                 330                 335

Ser Ala Arg Asn Ser Gly Arg Asn Gly Thr Ser Thr Ser Gly Gly
            340                 345                 350
```

```
Gly Lys Gly Ser Arg Ser Ser Lys Arg Ser Gln Arg Trp Gln Ala Lys
        355                 360                 365
Arg Phe Arg Thr Glu Ala Lys Ala Thr Lys Thr Val Gly Thr Ile Val
        370                 375                 380
Gly Gly Phe Ile Cys Cys Trp Leu Pro Phe Phe Thr Val Tyr Leu Val
385                 390                 395                 400
Arg Ala Phe Cys Glu His Cys Ile Pro Asn Leu Leu Phe Ser Val Phe
                    405                 410                 415
Phe Trp Leu Gly Tyr Cys Asn Ser Ala Ile Asn Pro Leu Ile Tyr Val
                420                 425                 430
Leu Val Ser Lys Asp Phe Arg Leu Ala Phe Lys Arg Ile Leu Cys Arg
            435                 440                 445
Cys Arg Leu Lys Glu Gly Gly Val Ser Ser Leu Ile Lys Gln Ile His
        450                 455                 460
Met Leu Thr Val Leu Asp Asp Ala Pro Pro Asp Asn Ala Glu Ser Pro
465                 470                 475                 480

<210> SEQ ID NO 41
<211> LENGTH: 1443
<212> TYPE: DNA
<213> ORGANISM: Rhipicephalus saguineus

<400> SEQUENCE: 41
ctagggcgac tcggcgttgt ccggggggtgc gtcgtcaagt acggtgagca tgtggatctg      60
tttgatgagt gacgagacgc ctccttcttt gaggcggcag cgacacagga tgcgcttgaa     120
ggccagccga aagtccttgc tgacaagcac gtagatgagc gggttgatgg ccgagttgca     180
gtatccgagc cagaagaaga ccgagaacag caggttgggg atgcagtgct cgcagaatgc     240
acgcaccagg tacactgtga agaagggcag ccagcagcat ataaagccac ccacgatggt     300
gcccacggtc ttggtggcct tggcctctgt gcggaatcgc ttggcctgcc accgttgact     360
gcgtttgctc gaacgcgagc ccttgccgcc gcgctagac gtggaagtgc cgttgcgtcc     420
actgttgcgg gcgctgcccc tgttcgactt gaacgagggc ggcgccgagc gcgtggtccg     480
ctggtcactt tgctgacgcg tcttgctggc tgacgaccgg gcgctggctg acggctcgtc     540
gcgcgacttc ttgagtccgg gccggcgacg accggtgacg atgccatcga tgcaggtctc     600
agcaccgagg tgctcgctac ctcgcttggc gttcatagcg gaatcgttac gcgcggtgga     660
gcgtagcgtg agcctctggt ccgttgtgcg tcccttgatc tttcctgact tgtggttat     720 gaaacctcgt tcaagggcgc gcccagtctg atggctgcg cggtatatgc ggtagttgaa      780
aaacagcatg aacagcatcg gtatgtagaa agagcccaga gccgagtaga tgacgtagcc     840
cttgttgttt atcagcacac attgtgcgga cttgcagagc ggcaacgggc catcggcagc     900
gatgctcgaa ttgtgcaagg tctcgttcga cccgtggtaa ggcacgctgt tttgagaccc     960
gccgtcgttc catccaacga gcggcgggaa gcagatgaca aaggcgatca cccacaccgc    1020
cacgatgagc aacttggcgc ggcgcgacga catgaggctc cggtagcgaa ccggccgcgt    1080
gatggccaag tagcggtcca cgctgatggc gcagagattc aggatggatg atgtgcagag    1140
ccatacgtcc acagctagcc atatctggca ccaggtgtgg ccgaagatcc acacctcgag    1200
cacctccaac acaattgagt atggcaacac ggtgagccca accgagaggt cggccacagc    1260
caaggacacc acgaagtagt tggtgaccgt gcgcagcttt gttgaggcca gcacggcgat    1320
aatgaccagc aggttaccga agatgacgag tccattgatg agcccagta cgaagaacag    1380 ggccacagtg accggctcat ggagcttctc tggcggcacg cgggacaggc acgtctcgtt    1440
```

| | |
|---|---|
| cat | 1443 |

<210> SEQ ID NO 42
<211> LENGTH: 33
<212> TYPE: DNA
<213> ORGANISM: Artificial
<220> FEATURE:
<223> OTHER INFORMATION: Synthetic Primer

<400> SEQUENCE: 42

| | |
|---|---|
| gccatcatyg tgggcrkstt catcktbtgc tgg | 33 |

<210> SEQ ID NO 43
<211> LENGTH: 33
<212> TYPE: DNA
<213> ORGANISM: Artificial
<220> FEATURE:
<223> OTHER INFORMATION: Synthetic Primer

<400> SEQUENCE: 43

| | |
|---|---|
| gatcatsggr ttwayggcsg agttgcagta gcc | 33 |

<210> SEQ ID NO 44
<211> LENGTH: 23
<212> TYPE: DNA
<213> ORGANISM: Artificial
<220> FEATURE:
<223> OTHER INFORMATION: Synthetic Primer

<400> SEQUENCE: 44

| | |
|---|---|
| gctggctgcc attcttcacc gtg | 23 |

<210> SEQ ID NO 45
<211> LENGTH: 27
<212> TYPE: DNA
<213> ORGANISM: Artificial
<220> FEATURE:
<223> OTHER INFORMATION: Synthetic Primer

<400> SEQUENCE: 45

| | |
|---|---|
| ccatcctaat acgactcact atagggc | 27 |

<210> SEQ ID NO 46
<211> LENGTH: 24
<212> TYPE: DNA
<213> ORGANISM: Artificial
<220> FEATURE:
<223> OTHER INFORMATION: Synthetic Primer

<400> SEQUENCE: 46

| | |
|---|---|
| ggtgcgtgca ttctgcgagc actg | 24 |

<210> SEQ ID NO 47
<211> LENGTH: 24
<212> TYPE: DNA
<213> ORGANISM: Artificial
<220> FEATURE:
<223> OTHER INFORMATION: Synthetic Primer

<400> SEQUENCE: 47

| | |
|---|---|
| agaagaccga gaacagcagg ttgg | 24 |

<210> SEQ ID NO 48
<211> LENGTH: 29
<212> TYPE: DNA
<213> ORGANISM: Artificial
<220> FEATURE:

```
<223> OTHER INFORMATION: Synthetic Primer

<400> SEQUENCE: 48
tggcaccagg tgtggccgaa gagccacac                              29

<210> SEQ ID NO 49
<211> LENGTH: 24
<212> TYPE: DNA
<213> ORGANISM: Artificial
<220> FEATURE:
<223> OTHER INFORMATION: Synthetic Primer

<400> SEQUENCE: 49
atgaacgaga cgtgcctgtc ccgc                                   24

<210> SEQ ID NO 50
<211> LENGTH: 24
<212> TYPE: DNA
<213> ORGANISM: Artificial
<220> FEATURE:
<223> OTHER INFORMATION: Synthetic Primer

<400> SEQUENCE: 50
ctagggcgac gcggcgttgt ccgg                                   24
```